US011512316B2

(12) United States Patent
Daley et al.

(10) Patent No.: US 11,512,316 B2
(45) Date of Patent: Nov. 29, 2022

(54) ENHANCED ORGANOGENESIS THROUGH MANIPULATION OF LIN28/LET-7/DIS3L2

(71) Applicant: Children's Medical Center Corporation, Boston, MA (US)

(72) Inventors: George Q. Daley, Cambridge, MA (US); Alena V. Yermalovich, Cambridge, MA (US); Jihan K. Osborne, Brighton, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 16/622,130

(22) PCT Filed: Jun. 14, 2018

(86) PCT No.: PCT/US2018/037649
§ 371 (c)(1),
(2) Date: Dec. 12, 2019

(87) PCT Pub. No.: WO2018/232191
PCT Pub. Date: Dec. 20, 2018

(65) Prior Publication Data
US 2020/0123549 A1 Apr. 23, 2020

Related U.S. Application Data

(60) Provisional application No. 62/519,822, filed on Jun. 14, 2017.

(51) Int. Cl.
*C12N 15/11* (2006.01)
*C12N 15/113* (2010.01)
*A61P 13/12* (2006.01)
*A61K 9/00* (2006.01)
*A61K 38/17* (2006.01)
*A61K 48/00* (2006.01)

(52) U.S. Cl.
CPC ........ *C12N 15/1137* (2013.01); *A61K 9/0034* (2013.01); *A61K 38/1709* (2013.01); *A61P 13/12* (2018.01); *A61K 48/00* (2013.01); *C12N 2310/11* (2013.01); *C12N 2310/14* (2013.01); *C12N 2320/32* (2013.01)

(58) Field of Classification Search
CPC ............ C12N 15/113; C12N 2310/141; C12N 2320/50; C12N 15/111; C12N 2310/14; C12N 2310/11; C12N 2310/113; A61K 31/713
See application file for complete search history.

(56) References Cited

U.S. PATENT DOCUMENTS

| 2008/0090765 A1 | 4/2008 | Schmidt-Ott et al. |
| 2011/0008892 A1 | 1/2011 | Nigam et al. |
| 2012/0045395 A1* | 2/2012 | Kaminski ............ C12Q 1/6883 424/9.1 |
| 2014/0221463 A1* | 8/2014 | Aguirre ................ A61K 31/713 514/44 R |
| 2019/0093106 A1* | 3/2019 | Dey ...................... C12N 15/113 |
| 2019/0111179 A1* | 4/2019 | Gu .......................... A61L 27/22 |

OTHER PUBLICATIONS

Vinas et al., miRNA let-7e modulates the Wnt pathway and early nephrogenic markers in mouse embryonic stem cell differentiation, PLOS ONE, vol. 8, issue 4, e60937, pp. 1-8. (Year: 2013).*
Phua et al., Data descriptor: small non-coding RNA expression in mouse nephrogenic mesenchymal progenitors, Scientific Dana, vol. 5:180218, pp. 1-11. (Year: 2018).*
Wang et al., Let-7d miRNA prevents TGF-beta1-induced EMT and renal fibrogenesis through regulation of HMGA2 expression, BBRC, vol. 479, pp. 676-682. (Year: 2016).*
Black et al., When birth comes early: Effects on nephrogenesis, Nephrology, vol. 18, pp. 180-182. (Year: 2013).*
Lichner et al., Obstacles in renal regenerative medicine: metabolic and epigenetic parallels between cellular reprogramming and kidney cancer oncogenesis, European Urology Focus, vol. 5, pp. 250-261. (Year: 2019).*
Seeger et al., Inhibition of let-7 augments the recruitment of epicardial cells and improves cardiac function after myocardial infarction, Journal of Molecular and Cellular Cardiology, vol. 94, pp. 145-152. (Year: 2016).*
Griepenburg et al., Caged oligonucleotides for bidirectional photomodulation of let-7 miRNA in zebrafish embryos, Bioorganic & Medicinal Chemistry, vol. 21, pp. 6198-6204. (Year: 2013).*
Wu et al., Precise let-7 expression levels balance organ regeneration against tumor suppression, eLife, vol. 4:e09431, pp. 1-16. (Year: 2015).*
Sene et al., Impact of gestational low-protein intake on embryonic kidney microRNA expression and in nephron progenitor cells of the male fetus, PLoS ONE, vol. 16(2):e0246289, pp. 1-24. (Year: 2021).*
Peng et al., Genome-wide studies reveal that Lin28 enhances the translation of genes important for growth and survival of human embryonic stem cells. Stem Cells. 2011;29(3):496-504.
Polesskaya et al., Lin-28 binds IGF-2 mRNA and participates in skeletal myogenesis by increasing translation efficiency. Genes Dev. 2007;21(9):1125-1138.
Qiu et al., Lin28-mediated post-transcriptional regulation of Oct. 4 expression in human embryonic stem cells. Nucleic Acids Res. 2010;38(4):1240-1248.
Rybak et al., A feedback loop comprising lin-28 and let-7 controls pre-let-7 maturation during neural stem-cell commitment. Nat Cell Biol. 2008;10(8):987-993.

(Continued)

*Primary Examiner* — Dana H Shin
(74) *Attorney, Agent, or Firm* — Wolf, Greenfield & Sacks, P.C.

(57) ABSTRACT

Described herein are methods of prolonging or reactivating organogenesis in a subject in need thereof (e.g., a subject that has impaired organ function such as a prematurely born infant). The methods comprise increasing the expression or activity of Lin28A or Lin28B proteins, inhibiting the expression or activity of let-7 family microRNAs, and/or inhibiting the expression or activity of Dis3L2 exonuclease.

10 Claims, 31 Drawing Sheets

Specification includes a Sequence Listing.

(56) References Cited

OTHER PUBLICATIONS

Urbach et al., Lin28 sustains early renal progenitors and induces Wilms tumor. Genes Dev. May 1, 2014;28(9):971-82. doi: 10.1101/gad.237149.113. Epub Apr. 14, 2014.
Yang et al., Temporally regulated expression of Lin-28 in diverse tissues of the developing mouse. Gene Expr Patterns. 2003;3(6):719-726.
PCT/US18/37649, dated Nov. 23, 2018, International Search Report and Written Opinion.
PCT/US18/37649, dated Dec. 26, 2019, International Preliminary Report on Patentability.
Barnett et al., Low birth weight is associated with impaired murine kidney development and function. Pediatr Res. Aug. 2017;82(2):340-348.
Boubred et al., The magnitude of nephron number reduction mediates intrauterine growth-restriction-induced long term chronic renal disease in the rat. A comparative study in two experimental models. J Transl Med. Nov. 30, 2016;14(1):331.
Jiang, A Regulator of Metabolic Reprogramming: MicroRNA Let-7. Transl Oncol. Jul. 2019;12(7):1005-1013.

* cited by examiner

NC = negative control (wild-type gDNA)
NTC = non-template control (H2O)

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 1
gcaagtcagc aactggttca                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 2
cttctcatcc tcggaactgc                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 3
tttccctggg actacgaatg                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 4
ggaaagccat ctgttccaaa                                              20

<210> SEQ ID NO 5
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 5
tactcctgct tgctgatcca c                                            21

<210> SEQ ID NO 6
<211> LENGTH: 24
<212> TYPE: DNA
<213> ORGANISM: Artificial Sequence
```

```
<220> FEATURE:
<223> OTHER INFORMATION: Synthetic Polynucleotide

<400> SEQUENCE: 6
cagaaggaga ttactgctct ggct                                    24

<210> SEQ ID NO 7
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 7
gccccttgga tattccagtc                                         20

<210> SEQ ID NO 8
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 8
tgactcaagg cctttggaag                                         20

<210> SEQ ID NO 9
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 9
tttggctgag gaggtagact gcat                                    24

<210> SEQ ID NO 10
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 10
atggatcaga tgtggactgt gcga                                    24

<210> SEQ ID NO 11
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 11
agcttgcatt ccttggcatg atgg                                    24

<210> SEQ ID NO 12
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 12
aggcggtgga gttcaccttt aaga                                    24
```

```
<210> SEQ ID NO 13
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 13
cacaacgggt tcttctgtta gtcc                                          24

<210> SEQ ID NO 14
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 14
caggtccatg ctggtattgc attgctc                                       27

<210> SEQ ID NO 15
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 15
catgctggta ttgcattgct ctgtcagcag                                    30

<210> SEQ ID NO 16
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 16
cacacctccc cctgaacctg aaac                                          24

<210> SEQ ID NO 17
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 17
caatgctgca atccattctc tccacctcac                                    30

<210> SEQ ID NO 18
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 18
caaccttctc cactgcatac cacggcaatc                                    30
```

ENHANCED ORGANOGENESIS THROUGH MANIPULATION OF LIN28/LET-7/DIS3L2

RELATED APPLICATIONS

This application is a national stage filing under 35 U.S.C. § 371 of International application number PCT/US2018/037649 filed Jun. 14, 2018, which claims the benefit under 35 U.S.C. § 119 of U.S. Provisional Application No. 62/519,822, filed Jun. 14, 2017, and entitled "ENHANCED ORGANOGENESIS THROUGH LIN28/LET-7-MEDIATED REPROGRAMMING", the entire contents of each of which are incorporated herein by reference.

GOVERNMENT LICENSE RIGHTS

This invention was made with government support under Grant nos. GM107536 and CA212487, awarded by the National Institutes of Health. The government has certain rights in the invention.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Dec. 12, 2019, is named C123370124US01-SEQ-RE and is 3.83 kilobytes in size.

BACKGROUND

Babies delivered prematurely or suffered intrauterine growth restriction are associated with many major complications mostly at birth, but also throughout maturity including infection, acute intestinal inflammation, acute and chronic lung disease, and low nephron endowment. Infants born too early are almost always placed on the steroid, dexamethasone, to speed up the process of lung and kidney development, which leads to a host of side effects.

SUMMARY

Provided herein are methods of manipulating the Lin28/let-7 axis to expand the number of progenitor cells that properly differentiate into functional units of embryonic organs (e.g., embryonic kidney). In some embodiments, the method comprises increasing the expression or activity of Lin28A and/or Lin28B. In some embodiments, the method comprises inhibiting the expression or activity of several microRNAs from the let-7 microRNA family (e.g., let-7a-1, let-7a-2, let-7a-3, let-7b, let-7c, let-7d, let-7e, let-7f-1, let-7f-2, let-7g, let-7i, and miR-98). In some embodiments, the let-7 microRNAs are inhibited pharmacologically, e.g., using antagomirs. The methods described herein may be used to prolong or reactivate the period of organogenesis of various organs (e.g., brain, intestine, heart, stomach, kidney, and lung) in children suffering from the complications of premature birth and/or intrauterine growth restriction.

Accordingly, some aspects of the present disclosure provide methods of prolonging or reactivating organogenesis, the method comprising administering to a subject in need thereof an effective amount of an agent that: (i) increases the expression or activity of Lin28A or Lin28B; (ii) inhibits the expression or activity of a let-7 microRNA; and or (iii) inhibits the expression or activity of Dis3L2.

In some embodiments, the agent increases the expression or activity of Lin28B. In some embodiments, the agent comprises a nucleic acid molecule comprising a nucleotide sequence encoding Lin28A or Lin28B operably linked to a promoter.

In some embodiments, the agent is a let-7 inhibitor. In some embodiments, the agent inhibits expression of the let7 microRNA. In some embodiments, the agent inhibits the activity of the let-7 microRNA. In some embodiments, the let7 inhibitor comprises an antagomir, an oligonucleotide, or a small molecule. In some embodiments, the let-7 microRNA is selected from the group consisting of: let-7a-1, let-7a-2, let-7a-3, let-7b, let-7c, let-7d, let-7e, let-7f-1, let-7f-2, let-7g, let-7i, miR-98, and combinations thereof.

In some embodiments, the agent inhibits the expression of Dis3L2. In some embodiments, the agent that inhibits the expression of Dis3L2 is an RNA interference (RNAi) molecule or an antisense nucleic acid. In some embodiments, the agent inhibits the activity of Dis3L2.

In some embodiments, the subject is human. In some embodiments, the subject is a human infant. In some embodiments, the human infant is born prematurely.

In some embodiments, the subject suffers from intrauterine growth restriction. In some embodiments, the subject is malnourished.

In some embodiments, the agent is delivered systemically. In some embodiments, the agent increases the expression or activity of Lin28A or Lin28B systemically; or inhibits the expression or activity of a let-7 microRNA systemically. In some embodiments, the agent is administered directly to an organ. In some embodiments, the agent increases the expression or activity of Lin28A or Lin28B in the organ; or inhibits the expression or activity of a let-7 microRNA in the organ.

In some embodiments, the organ is selected from the group consisting of brain, intestine, heart, stomach, kidney, and lung. In some embodiments, the organ is a kidney.

In some embodiments, the agent increases the number of functional nephrons in the kidney. In some embodiments, the agent improves organ function.

Further provided herein are methods of prolonging organogenesis in an embryonic organ, the method comprising: (i) increasing the expression or activity of Lin28A or Lin28B in the embryonic organ; (ii) inhibiting the expression or activity of a let-7 microRNA in the embryonic organ; and or (iii) inhibiting the expression or activity of Dis3L2.

In some embodiments, the expression or activity of Lin28B is increased. In some embodiments, a nucleic acid molecule comprising a nucleotide sequence encoding Lin28A and/or Lin28B operably linked to a promoter is delivered to a cell of the embryonic organ.

In some embodiments, the expression or activity of the let7 microRNA is inhibited. In some embodiments, a let7 inhibitor is delivered to a cell of the embryonic organ.

In some embodiments, the let7 inhibitor comprises an antagomir, an oligonucleotide, or a small molecule. In some embodiments, the let-7 microRNA is selected from the group consisting of: let-7a-1, let-7a-2, let-7a-3, let-7b, let-7c, let-7d, let-7e, let-7f-1, let-7f-2, let-7g, let-7i, miR-98, and combinations thereof.

In some embodiments, the expression of Dis3L2 is inhibited. In some embodiments, the expression of Dis3L2 is inhibited by an RNA interference (RNAi) molecule or an antisense nucleic acid. In some embodiments, the the activity of Dis3L2 is inhibited.

In some embodiments, the embryonic organ is selected from the group consisting of brain, intestine, heart, stomach, kidney, and lung. In some embodiments, the embryonic organ is a kidney.

In some embodiments, the number of progenitor cells in the embryonic organ increases. In some embodiments, the progenitor cells differentiate into functional glomeruli. In some embodiments, organ function improves.

Other aspects of the present disclosure provide compositions comprising an effective amount of an agent that: (i) increases the expression or activity of Lin28A or Lin28B; (ii) inhibits the expression or activity of a let-7 microRNA; and/or (iii) inhibits the expression or activity of Dis3L2, for use in prolonging or reactivating organogenesis in an subject in need thereof. In some embodiments, the composition further comprises a pharmaceutically acceptable carrier.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. The patent or application file contains at least one drawing executed in color. Copies of this patent or patent application publication with color drawing(s) will be provided by the Office upon request and payment of the necessary fee. In the drawings:

(FIG. 1A) Western blot analysis against LIN28A, LIN28B and SIX2 in lysates collected from dissected embryonic (E), Newborn (NB), postnatal (P) and adult wild-type kidneys at the indicated developmental time points. (FIG. 1B) Absolute quantitative real-time PCR (qRT-PCR) analysis measuring the levels of Lin28A and Lin28B in wild-type kidneys. Data are mean±SD; n=3 from each sample type. (FIGS. 1C and 1D) Relative qRT-PCR analysis measuring the levels of mature and precursor let-7 microRNAs in wild-type kidneys. Data are mean±SD; n=3-5 from each sample type.

(FIGS. 2A and 2B) Relative qRT-PCR analysis measuring the levels of mature and precursor let-7 microRNAs in wild-type kidneys at the indicated developmental time points. Data are mean±SD; n=3-5 from each sample type.

(FIG. 3A) qRT-PCR conducted on two cohorts of: intestine, stomach, liver, heart, brain from ages E12.5 to E18.5 and three cohorts of lungs from ages E11.5 to adult using standard designed around exon 2 for Lin28A and Lin28B. (FIG. 3B) Immunoblots for protein expression from one of three cohorts of lung as mentioned above from ages E12.5-E18.5 and mESCs as control conducted for Lin28A, Lin28B and tubulin. (FIG. 3C) Immunoblots for protein expression looking at embryonic expression of Lin28 brain (Yang and Moss, 2003) and intestine (Tu et al., 2015).

(FIGS. 5A, 5C, 5D, and 5F) Relative qRT-PCR analysis measuring the levels of LIN28B, mature let-7, Six2 and Eya1 respectively in iLIN28B and control kidneys at the indicated developmental time points. Data are mean±SD; n=3 from each genotype; the animals are littermates at each time point. (FIGS. 5B, 5E, and 5G) Representative immunohistochemistry staining against LIN28B, Six2, Eya1 respectively in iLIN28B and control kidneys.

(FIG. 6A) Representative images of iLIN28B and littermate control kidneys from E18.5 to 3 months old animals. Bar, 10 mm. (FIGS. 6B and 6C) Kidney weight and body weight of iLin28B and control mice. Data are mean±SD; n=3-8 from each genotype; the animals are littermates from one or two different litters at each time point. (FIG. 6D) Representative H&E image of 1 month old transgenic and littermate control kidneys. Arrows point to glomerulus-like structures. (FIG. 6E) Average number of glomeruli per 4× magnification field in the microscope; the slides were coded and the counting was carried out blind. (FIGS. 6F and 6G) Glomerular filtration rate (GFR) and creatinine levels of iLIN28B and littermate control animals. Measured blindly. Data are mean±SD; n=14 from each genotype; each group contains mice from three different litters. (FIGS. 6H and 6I) GFR and creatinine levels of iLIN28B and littermate control animals on low-protein (LP) diet. Measured blindly. Data are mean±SD; n=4-8 from each genotype; each group contains mice from two different litters. (Regular diet has been described in FIGS. 6F and 6G and is shown for comparison).

(FIGS. 7A, 7B, and 7D) Relative qRT-PCR analysis measuring the levels of mature let-7a,-f,-d; Six2; Eya1 respectively in let-7 (let-7a-1; let-7f-1; let-7d) cluster KO (let-7 KO) mice and wild type (WT) littermates at the indicated developmental time points. Data are mean±SD; n=2-6 from each genotype. (FIGS. 7C and 7E) Representative immunohistochemistry staining against Six2, Eya1, respectively, in let-7 KO mice and WT littermates. (FIG. 7F) Representative whole-mount immunofluorescence staining against Six2 for the P1 let-7 KO and WT kidneys. Bar, 500 um. FIGS. 7G and 7H) The number of niches and the number of progenitors per niche, respectively, at P1. Data are mean±SD; n=7 for each genotype; each group contains mice from 3 different litters. (FIGS. 7I and 7J) Kidney weight and body weight of let-7 KO mice and WT littermates. Data are mean±SD; n=2-6 from each genotype. (FIGS. 7K and 7L) GFR and creatinine levels of the let-7 KO and WT littermate controls. Measured blindly in 2-3 month old animals. Data are mean±SD; n=6-13 from each genotype; each group contains mice from 2-3 different litters.

(FIG. 10A) Dis3l2 transgene allele map and breeding schematic. (FIG. 10B) Dis3l2 allele genotyping (targeting validation).

(FIG. 11A) Mortality rate of Dis3l2 wild type, heterozygous, and knockout littermates at E18.5. n=21-57 embryos; each group contains mice from 8 different litters. (FIG. 11B) Representative image of E18.5 Dis3l2 knockout and littermate control embryos. Scale bar, 1 cm. (FIG. 11C) Body weight of Dis3l2 wild type, heterozygous, and knockout littermates at E18.5. Data represents mean±SD; n=26-57 embryos from each genotype. P>0.05 by unpaired, 2-tailed Student's t-test. (FIG. 11D) Kidney weight (left panel) of littermates at E18.5 normalized to body weight. Data are mean±SD; n=26-57 from each genotype. ****p≤0.001 by unpaired, 2-tailed Student's t-test. Representative image of Dis3l2 knockout and wild type littermate control kidneys (right panel). Scale bar, 5 mm. (FIG. 11E) Representative H&E image of E18.5 Dis3l2 knockout and wild type littermate control kidneys showing proximal and distal (dt) tubules (scale bar, 400 µm). (FIG. 11/) LacZ immunohistochemistry analysis representing Dis3l2 expression (dark grey) in differentiated proximal and distal tubules (tubs) of the E18.5 embryonic kidneys. In the absence of Dis3l2 expression in undifferentiated mesenchymal cells (mes). Inset rectangle in the left panel was enlarged in the right panel. Nuclei were counterstained with Hematoxylin (scale bars, 400 µm). (FIG. 11G) Western blotting of renal progenitor markers in E18.5 embryonic kidneys.

(FIG. 12B) from E15.5 organs 24 hrs post intraperitoneal injection of antagomirs or miRNA inhibitor negative control.

DETAILED DESCRIPTION OF CERTAIN EMBODIMENTS

Figure 1A:
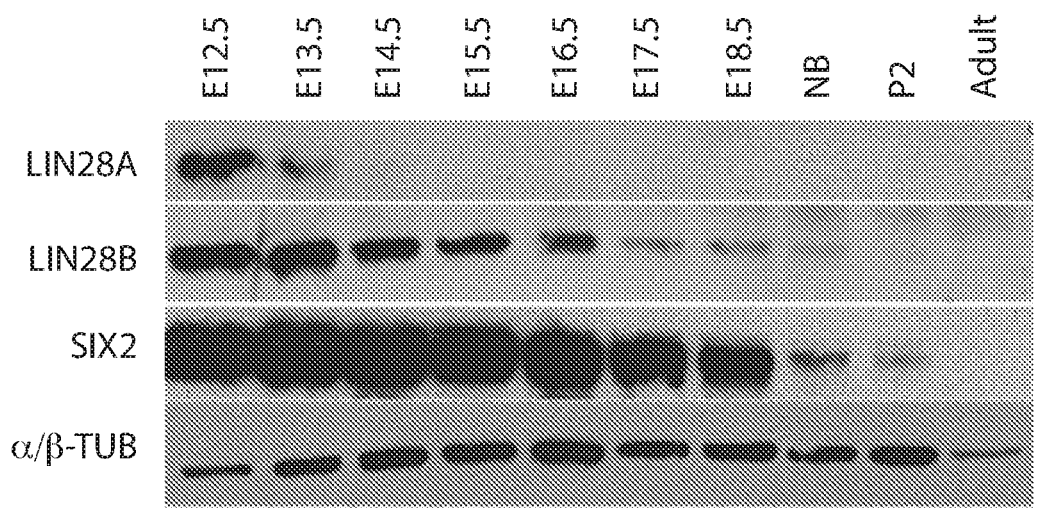
FIGS. 1A to 1D. Analysis of endogenous expression of Lin28 and let-7 in mouse embryonic kidney.

Lin28 is a highly conserved RNA-binding protein that regulates one of the most ancient microRNA (microRNA) families, let-7, by binding to the terminal loops of the precursors and blocking their processing to mature microRNAs. The mammalian genome encodes two Lin28 paralogs, Lin28A and Lin28B, which are both responsible for suppression of let-7 microRNA biogenesis. It was recently demonstrated that loss of both Lin28A and Lin28B in the whole body of the mouse resulted in embryonic lethality between embryonic (E) days 10.5 and 12.5. Lin28A and Lin28B have been shown to highly expressed from early embryogenesis throughout mid-late gestation in several tissues including kidney, lung and brain. During normal development, Lin28 is highly expressed early in the stem and progenitor cells, where the let-7 family of microRNAs is present in low amounts or absent. As progenitor cells differentiate, Lin28 expression decreases, allowing formation of mature let-7 microRNAs. In return, let-7 microRNAs inhibit the expression of genes involved in self-renewal, resulting in differentiation and lineage commitment.

It is demonstrated herein that genetic manipulation of the Lin28/let-7 axis expands the number of progenitor cells that properly differentiate into functional units of embryonic organs (e.g., embryonic kidney) and improve organ (e.g., kidney) function. Accordingly, some aspects of the present disclosure provide methods of prolonging or reactivating organogenesis, by: (i) increasing the expression or activity of Lin28A or Lin28B; and/or (ii) inhibiting the expression or activity of a let-7 microRNA. In some embodiments, the organogenesis of an organ in a subject (e.g., a premature infant) is reactivated by the methods described herein. In some embodiments, the methods comprise administering to a subject in need thereof an effective amount of an agent that: (i) increases the expression or activity of Lin28A or Lin28B; (ii) inhibits the expression or activity of a let-7 microRNA; and/or inhibits the expression or activity of Dis3L2. In some embodiments, the methods are used to prolong organogenesis in an embryonic organ (e.g., a human embryonic organ). As such, the agent may be delivered to a cell of the embryonic organ. In some embodiments, prolonging or reactivating organogenesis improves organ function (e.g., in a subject or in an embryonic organ).

"Organogenesis" refers to a process in animal development by which the ectoderm, endoderm and mesoderm develop into the internal organs of the organism. The endoderm produces tissue within the lungs, thyroid, and pancreas. The mesoderm aids in the production of cardiac muscle, skeletal muscle, smooth muscle, tissues within the kidneys, and red blood cells. The ectoderm produces tissues within the epidermis and aids in the formation of neurons within the brain, and melanocytes.

In humans, organogenesis begins around the 3rd to 8th week in utero. The organogenesis process differs between each organ (e.g., brain, intestine, heart, stomach, kidney and lung) and takes different periods of time to reach completion. During organogenesis, progenitor cells differentiate and commit to a certain lineage, forming functional units of an organ. For example, the functional units of kidney, termed "nephrons," which are responsible for the filtration function of the kidney, form only during development in utero, and reach completion at approximately 34-36 weeks of gestation. One skilled in the art is familiar with the normal period of organogenesis (e.g., human organogenesis) for an organ (e.g., brain, intestine, heart, stomach, kidney and lung).

In some embodiments, the process of organogenesis may be manipulated using the methods described herein such that the period of organogenesis is prolonged. "Prolong organogenesis" means that the period of organogenesis is extended, compared to the normal period of organogenesis for a certain organ. Prolonging organogenesis occurs before the organogenesis process reaches completion. As such, in some embodiments, the process of prolonging organogenesis occurs in an embryonic organ (e.g., an embryonic brain, intestine, heart, stomach, kidney, or lung). In some embodiments, the process of prolonging organogenesis occurs in an embryonic kidney. To prolong the organogenesis process in an embryonic organ, in some embodiments, the agent may be delivered to a cell of the embryonic organ. One skilled in the art is familiar with methods of delivering an agent to a cell in an organ.

In some embodiments, the period of organogenesis is extended by at least 10%, compared to the normal period of organogenesis for a certain embryonic organ. For example, the period of organogenesis may be extended by at least 10%, at least 20%, at least 30%, at least 40%, at least 50%, at least 60%, at least 70%, at least 80%, at least 90%, at least 100%, or more, compared to the normal period of organogenesis for a certain embryonic organ. In some embodiments, the period of organogenesis may be extended by 10%, 20%, 30%, 40%, 50%, 60%, 70%, 80%, 90%, 100%, or more, compared to the normal period of organogenesis for a certain embryonic organ. In some embodiments, the period of organogenesis may be extended by at least 1 hour, a least 2 hours, at least 5 hours, at least 12 hours, at least 24 hours, at least 2 days, at least 5 days, at least 10 days, at least 20 days, at least 30 days, at least 40 days, at least 50 days, at least 60 days, at least 70 days, at least 80 days, at least 90 days, at least 100 days, or more, compared to the normal period of organogenesis for a certain embryonic organ. In some embodiments, the period of organogenesis may be extended by 1 hour, 2 hours, 5 hours, 12 hours, 24 hours, 2 days, 5 days, 10 days, 20 days, 30 days, 40 days, 50 days, 60 days, 70 days, 80 days, 90 days, 100 days, or more, compared to the normal period of organogenesis for a certain embryonic organ.

In some embodiments, the process of organogenesis is manipulated such that the process is reactivated after it has reached completion. "Reactivate organogenesis" means the process of organogenesis restarts after it has reached completion. In some embodiments, the organogenesis process may be reactivated 1 hour, 2 hours, 5 hours, 12 hours, 24 hours, 2 days, 5 days, 10 days, 20 days, 30 days, 40 days, 50 days, 60 days, 70 days, 80 days, 90 days, 100 days, or more, after the normal organogenesis process has reached completion.

Prolonging and/or reactivating organogenesis may be achieved by increasing the number of progenitor cells that are able to differentiate into functional units of a certain organ (e.g., nephrons of the kidney), which may be achieved by genetically manipulating the LIN28/let7 axis, as demonstrated herein. In some embodiments, the methods of prolonging organogenesis or reactivating organogenesis comprises increasing the expression or activity of Lin28A or Lin28B in a subject in need thereof, or in an embryonic organ. In some embodiments, the expression or activity of Lin28B is enhanced in a subject in need thereof, or in an embryonic organ. In some embodiments, the methods of prolonging organogenesis or reactivating organogenesis comprises inhibiting the expression or activity of a let-7 microRNA. In some embodiments, the let-7 microRNA is selected from the group consisting of: let7-a1, let7-f1, let7-f2, let7-g1, let7-i1, and combinations thereof.

"LIN28" is a RNA-binding protein that regulates gene expression partially via Let7 biogenesis. The Let7 family of microRNAs regulates many factors that control cell-fate decision, including oncogenes (c-myc, Ras, HMGA-2) and cell-cycle factors (CyclinD1, D2). In mammals, LIN28A and its closely related paralog LIN28B are highly expressed in pluripotent cells, where they play an important role in the maintenance of self-renewal and proliferation. There are two Lin28 paralogs in mammals: Lin28A (Lin28) and Lin28B, e.g., as described in Guo et al., 384 Gene 51 (2006); Lehrbach et al., 16 Nat. Str. Mol. Biol. 1016 (2009); Moss et al., 1997; Van Wynsberghe et al., 18 Nat. Str. Mol. Biol 302 (2011); and Viswanathan et al., 2010, incorporated herein by reference. Lin28B has also been shown to regulate expression of multiple let-7 family members, and genomewide association studies (GWAS) have linked Lin28B with the determination of human height, as well as control of the age of onset of puberty and menopause. Lin28B (and less frequently Lin28A) contribute to oncogenesis by coordinately inactivating multiple let-7 family microRNAs. Iliopoulos et al., 2009; Viswanathan et al., 2009. This finding is consistent with the fact that activation of Lin28A/Lin28B occurs in many different primary human tumors with an overall frequency of 15% and these tumors display downregulation let-7 expression, suggesting an important role in tumorigenesis. Indeed Lin28A/Lin28B are classical oncogenes that can promote cellular transformation when ectopically expressed. Iliopoulos et al., 2009; Viswanathan et al., 41 Nat. Genet. 843 (2009); West et al., 460 Nature 909 (2009). Importantly, this effect can be abrogated when let-7 is reintroduced into these cells. Iliopoulos et al., 2009; Viswanathan et al., 2009. Therefore, Lin28 mediated cellular transformation is directly dependent on let-7 levels.

"Let-7 microRNA" refers let-7 miRNA family members and homologues and variants thereof that do not adversely affect the structure or function. For example, let-7 refers to a let-7 family member from humans, including but not limited to let-7a-1, let-7a-2, let-7a-3, let-7b, let-7c, let-7d, let-7e, let-7f-1, let-7f-2, let-7g, let-7i, and miR-98 (e.g., as described in Riysg et al., Cell Reports, Volume 13, Issue 2, 13 Oct. 2015, Pages 260-266, incorporated herein by reference), and biologically active sequence variants of let-7, including alleles, and in vitro generated derivatives of let-7 that demonstrate let-7 activity.

Let-7 family microRNAs were first discovered as a key developmental regulator and became one of the first known microRNAs. The mature form of let-7 family members is highly conserved across species. In vertebrates (e.g., a mammal such as a human), the let-7 family has many members and the sequences, expression timing, as well as genomic clustering of these microRNAs members are all conserved across species. The direct role of let-7 family microRNAs in vertebrate development remains unclear.

The relationship between Lin28 proteins and the expression of microRNA let-7 (herein referred to as the "Lin28/let-7 axis") plays a role in normal mammalian development and stem cell pluripotency, e.g., as described in Viswanathan et al., 140 Cell 445 (2010), incorporated herein by reference. In embryonic cells, the RNA-binding protein Lin28 coordinately represses the let-7 family of microRNAs by binding to the terminal loop of pre- and pri-let-7 microRNAs, thereby inhibiting let-7 biogenesis, e.g., as described in Heo et al., 32 Mol. Cell 276 (2008); Newman et al., 14 RNA 1539 (2008); Rybak et al., 10 Nat. Cell Biol. 987 (2008); and Viswanathan et al., 320 Science 320 (2008), incorporated herein by reference. As cells undergo differentiation, Lin28 levels decrease, leading to a corresponding increase in mature let-7, which is retained in many adult tissues. As such, the posttranscriptional regulation of let-7 expression by Lin28 contributes to the maintenance of the pluripotent state by preventing let-7 mediated ES cell differentiation, e.g., as described in Martinez et al., 7 Cell 31 (2010), incorporated herein by reference. Furthermore, Lin28 mRNA is repressed by let-7 microRNAs, leading to an inversely correlated expression pattern between let-7 and Lin28 and a double negative feedback loop that controls cell differentiation, e.g., as described in Wu et al., 25 Mol. Cell Biol (2005), incorporated herein by reference.

In some embodiments, the method described herein comprises increasing the expression (gene product) or activity (biological function) of Lin28A or Lin28B (e.g., in a subject in need thereof or in an embryonic organ). In some embodiments, the method comprises administering to a subject in need thereof an effective amount of an agent that increases the expression or activity of Lin28A or Lin28B. In some embodiments, the agent increases the expression or activity of Lin28B. In some embodiments, the agent comprises a nucleic acid molecule comprising a nucleotide sequence encoding Lin28A or Lin28B, operably linked to a promoter. One skilled in the art is familiar with methods of supplying a cell with a nucleic acid molecule (e.g., an exogenous nucleic acid molecule such as a plasmid) encoding a protein of interest (e.g., Lin28A or Lin28B) to increase the expression of the protein of interest. In some embodiments, the increased expression is transient (i.e., only for a period of time, after which the expression level of the protein returns back to when the agent is absent). In some embodiments, the increased expression is permanent.

A "nucleic acid molecule" is at least two nucleotides covalently linked together, and in some instances, may contain phosphodiester bonds (e.g., a phosphodiester "backbone"). In some embodiments, the nucleic acid molecule is a vector. A "vector" is a nucleic acid molecule capable of transporting another nucleic acid to which it has been linked. Vectors capable of directing the expression of genes and/or nucleic acid sequence to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. Other expression vectors can be used in different embodiments of the invention, for example, but are not limited to, plasmids, episomes, bacteriophages or viral vectors, and such vectors can integrate into the host's genome or replicate autonomously in the particular cell. Other forms of expression vectors known by those skilled in the art which serve the equivalent functions can also be used. Expression vectors comprise expression vectors for stable or transient expression encoding the DNA. A vector can be a plasmid, bacteriophage, bacterial artificial chromosome or yeast artificial chromosome. A vector can be a DNA or RNA vector. A vector can be either a self-replicating extrachromosomal vector or a vector which integrates into a host genome. Viral vectors are commonly used for mammalian expression of an exogenous gene. Non-limiting examples of viral vectors that may be used in accordance with the present disclosure include lentiviral vectors, retroviral vectors, adeno-associated virus vectors, and any known viral vectors that may be used for gene delivery.

A promoter may be one naturally associated with a gene or sequence, as may be obtained by isolating the 5' non-coding sequences located upstream of the coding segment of a given gene or sequence. Such a promoter can be referred to as "endogenous." In some embodiments, a coding nucleic acid sequence may be positioned under the control of a recombinant or heterologous promoter, which refers to a promoter that is not normally associated with the encoded sequence in its natural environment. Such promoters may include promoters of other genes; promoters isolated from any other cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR) (see U.S. Pat. Nos. 4,683,202 and 5,928,906).

In some embodiments, a promoter is an "inducible promoter," which refers to a promoter that is characterized by regulating (e.g., initiating or activating) transcriptional activity when in the presence of, influenced by or contacted by an inducer signal. An inducer signal may be endogenous or a normally exogenous condition (e.g., light), compound (e.g., chemical or non-chemical compound) or protein that contacts an inducible promoter in such a way as to be active in regulating transcriptional activity from the inducible promoter. Thus, a "signal that regulates transcription" of a nucleic acid refers to an inducer signal that acts on an inducible promoter. A signal that regulates transcription may activate or inactivate transcription, depending on the regulatory system used. Activation of transcription may involve directly acting on a promoter to drive transcription or indirectly acting on a promoter by inactivating a repressor that is preventing the promoter from driving transcription. Conversely, deactivation of transcription may involve directly acting on a promoter to prevent transcription or indirectly acting on a promoter by activating a repressor that then acts on the promoter.

The administration or removal of an inducer signal results in a switch between activation and inactivation of the transcription of the operably linked nucleic acid sequence. Thus, the active state of a promoter operably linked to a nucleic acid sequence refers to the state when the promoter is actively regulating transcription of the nucleic acid sequence (i.e., the linked nucleic acid sequence is expressed). Conversely, the inactive state of a promoter operably linked to a nucleic acid sequence refers to the state when the promoter is not actively regulating transcription of the nucleic acid sequence (i.e., the linked nucleic acid sequence is not expressed).

An inducible promoter of the present disclosure may be induced by (or repressed by) one or more physiological condition(s), such as changes in light, pH, temperature, radiation, osmotic pressure, saline gradients, cell surface binding, and the concentration of one or more extrinsic or intrinsic inducing agent(s). An extrinsic inducer signal or inducing agent may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or combinations thereof.

Inducible promoters of the present disclosure include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some embodiments, an inducer signal of the present disclosure is an N-acyl homoserine lactone (AHL), which is a class of signaling molecules involved in bacterial quorum sensing. Quorum sensing is a method of communication between bacteria that enables the coordination of group based behavior based on population density. AHL can diffuse across cell membranes and is stable in growth media over a range of pH values. AHL can bind to transcriptional activators such as LuxR and stimulate transcription from cognate promoters. Other inducible promoter systems are known in the art and may be used in accordance with the present disclosure.

In some embodiments, the agent increases the expression or activity of Lin28A or Lin28B by at least 10%, compared to before the agent was administered. For example, the agent may increase the expression or activity of Lin28A or Lin28B by at least 10%, at least 20%, at least 30%, at least 40%, at least 50%, at least 60%, at least 70%, at least 80%, at least 90%, at least 100%, at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 60-fold, at least 70-fold, at least 80-fold, at least 90-fold, at least 100-fold, at least 1000-fold, or more, compared to before the agent is administered. In some embodiments, the agent increases the expression or activity of Lin28A or Lin28B by 10%, 20%, 30%, 40%, 50%, 60%, 70%, 80%, 90%, 100%, 2-fold, 3-fold, 4-fold, 5 fold-6-fold, 7-fold, 8-fold, 9-fold, 10-fold, 20-fold, 30-fold, 40-fold, 50-fold, 60-fold, 70-fold, 80-fold, 90-fold, 100-fold, 1000-fold, or more, compared to before the agent is administered. One skilled in the art is familiar with methods of evaluating protein expression level and activity, e.g., by western blotting, immunostaining, flow cytometry, and/or functional assays.

In some embodiments, the agent comprises a let-7 inhibitor. A "let-7 inhibitor" refers to an agent that inhibits the expression (gene product) of activity (biological function) of a let-7 microRNA. In some embodiments, the let-7 inhibitor inhibits the expression level or activity of a let-7 microRNA by at least 10%, compared to before the let-7 inhibitor was administered. For example, the let-7 inhibitor may inhibit the expression or activity of let-7 by least 10%, at least 20%, at least 30%, at least 40%, at least 50%, at least 60%, at least 70%, at least 80%, at least 90%, or 100%, compared to before the let-7 inhibitor is administered. In some embodiments, the let-7 inhibitor inhibits the expression or activity of let-7 by 10%, 20%, 30%, 40%, 50%, 60%, 70%, 80%, 90%, or 100%, compared to before the let-7 inhibitor is administered. One skilled in the art is familiar with methods of evaluating microRNA expression level and activity, e.g., by northern blotting, quantitative RT-PCR, and/or functional assays. In some embodiments, the let-7 inhibitor inhibits the expression or activity of a let-7 microRNA selected from the group consisting of: let7-a1, let7-f1, let7-f2, let7-g1, let7-i1, and combinations thereof.

Non-limiting examples of a let-7 inhibitor include antagomirs (or antimir), oligonucleotides, RNA interference molecule (e.g., siRNA, shRNA etc.), and small molecules. "Antagomirs (or miRNA inhibitors)" are small, chemically modified RNA molecules designed to specifically bind to and inhibit endogenous miRNA molecules and enable miRNA functional analysis by down-regulation of miRNA activity. Antagomirs can adopt a variety of configurations including single stranded, double stranded (RNA/RNA or RNA/DNA duplexes), and hairpin designs. In general, antagomirs comprise one or more sequences or portions of sequences that are complementary, or partially complementary, with the mature strand (or strands) of the microRNA to be targeted. In addition, a microRNA inhibitor can also comprise additional sequences located 5' and 3' to the sequence that is the reverse complement of the mature microRNA. The additional sequences can be the reverse complements of the sequences that are adjacent to the mature microRNA in the pre-microRNA, from which the mature microRNA is derived, or the additional sequences can be arbitrary sequences (having a mixture of A, G, C, U, or dT). In some embodiments, one or both of the additional sequences are arbitrary sequences capable of forming hairpins. Thus, in some embodiments, the sequence that is the reverse complement of the microRNA is flanked on the 5' side and on the 3' side by hairpin structures. MicroRNA inhibitors, when double stranded, can include mismatches between nucleotides on opposite strands.

Antagomirs, including hairpin antagomirs, are known in the art, e.g., as described in Vermeulen et al., 13 RNA 723-30 (2007); WO2007/095387; WO 2008/036825, incorporated herein by reference. A person of ordinary skill in the art can design an inhibitor directed to a let-7 microRNA that is useful for the methods disclosed herein. Antagomirs can include a phosphorothioate at least the first, second, or third internucleotide linkage at the 5' or 3' end of the nucleotide sequence. In one embodiment, antagomirs contain six phosphorothioate backbone modifications; two phosphorothioates are located at the 5'-end and four at the 3'-end. Phosphorothioate modifications provide protection against RNase activity and their lipophilicity contributes to enhanced tissue uptake.

Examples of antagomirs and other microRNA inhibitors are described in WO2009/020771, WO2008/091703, WO2008/046911, WO2008/074328, WO2007/090073, WO2007/027775, WO2007/027894, WO2007/021896, WO2006/093526, WO2006/112872, WO2007/112753, WO2007/112754, WO2005/023986, or WO2005/013901, incorporated herein by reference. Custom designed Anti-miR® molecules are commercially available from Applied Biosystems. Thus, in some embodiments, the antagomir is an Ambion® Anti-miR® inhibitor. Antagomirs can be chemically modified and optimized to specifically inhibit naturally occurring mature microRNA molecules in cells. Custom designed Dharmacon Meridian® microRNA Hairpin Inhibitors are also commercially available and can be obtained from Thermo Scientific. These inhibitors can include chemical modifications and secondary structure motifs. In some embodiments, secondary structural elements can be identified that can enhance the potency of an antagomir (e.g., as described in US2006/0223777, incorporated herein by reference). Other such improvements in antagomir design are also contemplated for use in the disclosed methods.

Let-7 antagomirs are commercially available. For example, Thermo Fisher Scientific company offers 1) Invitrogen™ Anti-miR™ miRNA Inhibitors or 2) Invitrogen™ mirVana™ miRNA Inhibitors (Cat. #4464088, used in the Examples provided herein) that both block biogenesis of let-7. In some embodiments, let-7 antagomirs may be synthesized. One skilled in the art is familiar with methods of synthesizing a let-7 antagomir.

An "oligonucleotide" let-7 inhibitor may be an anti-sense oligonucleotide that comprises a nucleotide sequence that is complementary to the nucleotide sequence of a let-7 microRNA.

RNA interference agents can be used with the methods described herein to inhibit the expression of let-7 microRNAs. "RNA interference (RNAi)" is an evolutionarily conserved process whereby the expression or introduction of RNA of a sequence that is identical or highly similar to a target gene results in the sequence specific degradation or specific posttranscriptional gene silencing (PTGS) of messenger RNA (mRNA) transcribed from that targeted gene (see Coburn, G. and Cullen, B., J. of Virology 76(18):9225 (2002), herein incorporated by reference in its entirety), thereby inhibiting expression of a let-7 microRNA. In general, RNA interference technology is well known in the art, as are methods of delivering RNA interfering agents. See, e.g., U.S. Patent Pub. No. 2010/0221226.

As used herein, "siRNA" is a class of double-stranded RNA molecules, which interferes with the expression of specific genes having a nucleotide sequence complementary to the siRNA. siRNAs typically have a well-defined structure: a short (e.g., 21 base pair) double-stranded RNA (dsRNA) with phosphorylated 5' ends and hydroxylated 3' ends with two overhanging nucleotides. The Dicer enzyme catalyzes production of siRNAs from long dsRNAs and small hairpin RNAs (shRNAs). An siRNA for use in accordance with the present disclosure may be about 15 to about 35 base pairs, or about 20 to about 25 base pairs, in length. In some embodiments, the siRNA may be about 15, 16, 17, 18, 19, 20, 21, 22, 23, 24, 25, 26, 27, 28, 29, 30, 31, 32, 33, 34 or 35 base pairs in length.

As used herein, "shRNA" refers to a sequence of RNA that makes a tight hairpin turn that can be used to silence target gene expression through RNA interference (RNAi). Expression of shRNA in cells may be accomplished by delivery of plasmids or through viral or bacterial vectors. For example, in some embodiments, shRNA targeting Dis3l2 may be delivered to an organ by injecting to the organ or by systemically injecting a plasmid contains a nucleic acid encoding the shRNA. In some embodiments, bacterial vectors may be used to obtain shRNA expression in cells. In some embodiments, viral vectors (e.g., adeno-associated viruses (AAVs), adenoviruses, and lentiviruses) may be used to obtain shRNA expression in cells.

A "small molecule" refers to a chemical agent including, but not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. Small molecules agents can be identified from within a small molecule library, which can be obtained from commercial sources such as AMRI (Albany, N.Y.), AsisChem Inc. (Cambridge, Mass.), TimTec (Newark, Del.), among others, or from libraries as known in the art.

In some embodiments, the agent comprises a Dis3L2 inhibitor. A "Dis3L2 inhibitor" refers to an agent that inhibits the expression (gene product) of activity (biological function) of the nuclease Dis3L2. Non-limiting examples of a Dis3L2 inhibitor include oligonucleotides (e.g., antisense nucleic acids), RNA interference molecule (e.g., siRNA, shRNA etc.), and small molecules. Agents that are known to inhibit the activities of exonucleases can also be used. Such agents include, without limitation, small molecules, inhibitory antibodies, and inhibitory peptides. Exonuclease inhibitors are also commercially available, e.g., from Tocris Biosciences.

"Dis3L2" is identified as a component of the Lin28/let-7 pathway and as the downstream nuclease responsible for the decay of uridylated pre-let-7. Dis3l2 belongs to a family of related 3'-5' exonucleases that include Dis3 and Dis3l1 with similar domain organization to bacterial RNase II (Astuti et al., 2012; Staals et al., 2010; Tomecki et al., 2010). Germline mutations in the Dis3l2 gene were recently found to be responsible for Perlman syndrome, a rare, autosomal recessive, fetal overgrowth syndrome (Astuti et al., 2012). In addition to being large, affected individuals are hypotonic, have organomegally, characteristic facial dysmorphism, renal abnormalities, neurodevelopmental problems, and a dramatically high susceptibility Wilms' tumors (Nephroblastoma) with >60% of surviving children developing (often bilateral) Wilms' tumors. Dis3l2 was found to be mutated in ~30% of sporadic Wilms' tumors analyzed with evidence also for loss of both Dis3l2 alleles (Astuti et al., 2012).

In some embodiments, the Dis3L2 inhibitor inhibits the expression level or activity of a let-7 microRNA by at least 10%, compared to before the Dis3L2inhibitor was administered. For example, the Dis3L2inhibitor may inhibit the expression or activity of Dis3L2 by least 10%, at least 20%, at least 30%, at least 40%, at least 50%, at least 60%, at least 70%, at least 80%, at least 90%, or 100%, compared to before the Dis3L2inhibitor is administered. In some embodiments, the let-7 inhibitor inhibits the expression or activity of Dis3L2by 10%, 20%, 30%, 40%, 50%, 60%, 70%, 80%, 90%, or 100%, compared to before the Dis3L2inhibitor is administered. One skilled in the art is familiar with methods of evaluating protein expression level and activity, e.g., by northern blotting, quantitative RT-PCR, and/or functional assays.

Thus, in some embodiments, the method described herein increases the number of progenitor cells in an embryonic organ (e.g., embryonic kidney). In some embodiments, the number of progenitor cell in an embryonic organ (e.g., embryonic kidney) is increased by least 10%, at least 20%, at least 30%, at least 40%, at least 50%, at least 60%, at least 70%, at least 80%, at least 90%, at least 100%, at least 2-fold, at least 3-fold, at least 4-fold, at least 5-fold, at least 6-fold, at least 7-fold, at least 8-fold, at least 9-fold, at least 10-fold, or more, compared to before the agent is delivered to a cell of an embryonic organ. In some embodiments, the number of progenitor cell in an embryonic organ (e.g., embryonic kidney) is increased by 10%, 20%, 30%, 40%, 50%, 60%, 70%, 80%, 90%, 100%, 2-fold, 3-fold, 4-fold, 5 fold-6-fold, 7-fold, 8-fold, 9-fold, 10-fold, or more, compared to before the agent is delivered to a cell of an embryonic organ.

In some embodiments, the method described herein improves organ function. "Improve organ function" means that the functionality of the organ (e.g., brain, intestine, heart, stomach, kidney, or lung) is improved by least 10%, at least 20%, at least 30%, at least 40%, at least 50%, at least 60%, at least 70%, at least 80%, at least 90%, at least 100%, at least 2-fold, at least 3-fold, at least 4-fold, at least 5-fold, at least 6-fold, at least 7-fold, at least 8-fold, at least 9-fold, at least 10-fold, or more, compared to before the agent is administered to the subject or delivered to a cell of an embryonic organ. In some embodiments, functionality of the organ (e.g., brain, intestine, heart, stomach, kidney, or lung) is improved by 10%, 20%, 30%, 40%, 50%, 60%, 70%, 80%, 90%, 100%, 2-fold, 3-fold, 4-fold, 5 fold-6-fold, 7-fold, 8-fold, 9-fold, 10-fold, or more, compared to before the agent is administered to the subject or delivered to a cell of an embryonic organ. In some embodiments, the organ is an embryonic organ. In some embodiments, the organ is in a subject. One skilled in the art is familiar with methods of evaluating the functionality of an organ.

In some embodiments, the organ is kidney and the progenitor cells differentiate into functional glomeruli and nephrons in the kidney (e.g., an embryonic kidney or a kidney in a subject). "Glomerulus" refers to a cluster of capillaries around the end of a kidney tubule, where waste products are filtered from the blood. A "nephron" is a functional unit in the kidney, consisting of a glomerulus and its associated tubule, through which the glomerular filtrate passes before emerging as urine. Nephrons are responsible for the filtration function of the kidney and form only during development in utero, and reach completion at approximately 34-36 weeks of gestation. Under normal circumstances, nephrons do not form postnatally. In some embodiments, the method described in increases the number of functional nephrons in the kidney by at least 10%. For example, the method described herein may increase the number of functional glomeruli and nephrons in the kidney by least 10%, at least 20%, at least 30%, at least 40%, at least 50%, at least 60%, at least 70%, at least 80%, at least 90%, at least 100%, at least 2-fold, at least 3-fold, at least 4-fold, at least 5-fold, at least 6-fold, at least 7-fold, at least 8-fold, at least 9-fold, at least 10-fold, or more, compared to before the agent is administered to the subject or delivered to a cell of an embryonic kidney. In some embodiments, the method described herein increases the number of functional glomeruli and nephrons in the kidney by 10%, 20%, 30%, 40%, 50%, 60%, 70%, 80%, 90%, 100%, 2-fold, 3-fold, 4-fold, 5 fold-6-fold, 7-fold, 8-fold, 9-fold, 10-fold, or more, compared to before the agent is administered to the subject or delivered to a cell of an embryonic kidney.

The number of functional nephrons in a kidney correlates with the function (e.g., filtration function) of the kidney. As such, the method described herein improves kidney (e.g., embryonic kidney or kidney in a subject) function by least 10%, at least 20%, at least 30%, at least 40%, at least 50%, at least 60%, at least 70%, at least 80%, at least 90%, at least 100%, at least 2-fold, at least 3-fold, at least 4-fold, at least 5-fold, at least 6-fold, at least 7-fold, at least 8-fold, at least 9-fold, at least 10-fold, or more, compared to before the agent is administered to the subject or delivered to a cell of an embryonic kidney (e.g., as measured by glomeruli filtration rate or GFR).

Other aspects of the present disclosure provide compositions comprising an effective amount of an agent that increases the expression or activity of Lin28A or Lin28B; inhibits the expression or activity of a let-7 microRNA, and/or inhibits Dis3L2 for use in prolonging or reactivating organogenesis in an subject in need thereof. In some embodiments, the composition comprises an effective amount of an agent that increases the expression or activity of Lin28A or Lin28B. In some embodiments, the composition comprises an effective amount of an agent that increases the expression or activity of Lin28B. In some embodiments, the composition comprises an effective amount of an agent that inhibits the expression or activity of a let-7 microRNA. In some embodiments, the composition comprises an agent that increases the expression or activity of Lin28A or Lin28B; and inhibits the expression or activity of a let-7 microRNA.

The composition can further comprise additional agents (e.g. for specific delivery, increasing half-life, or other therapeutic agents). In some embodiments, the composition further comprises a pharmaceutically acceptable carrier. The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. A "pharmaceutically acceptable carrier" is a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation.

Some examples of materials which can serve as pharmaceutically-acceptable carriers include, without limitation: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as peptides and amino acids (23) serum component, such as serum albumin, HDL and LDL; (24) C2-C12 alcohols, such as ethanol; and (25) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

An "effective amount" refers to the amount of agents required to confer therapeutic effect on the subject, either alone or in combination with one or more other therapeutic agents. Effective amounts vary, as recognized by those skilled in the art, depending on the particular condition being treated, the severity of the condition, the individual subject parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a subject may insist upon a lower dose or tolerable dose for medical reasons, psychological reasons or for virtually any other reasons.

Empirical considerations, such as the half-life, generally will contribute to the determination of the dosage. For example, therapeutic agents that are compatible with the human immune system, such as peptides comprising regions from humanized antibodies or fully human antibodies, may be used to prolong half-life of the agent and to prevent the agent being attacked by the host's immune system. Frequency of administration may be determined and adjusted over the course of therapy, and is generally, but not necessarily, based on treatment and/or suppression and/or amelioration and/or delay of a disorder. Alternatively, sustained continuous release formulations of agent may be appropriate. Various formulations and devices for achieving sustained release are known in the art.

An effective amount of the agent that increases the expression or activity of Lin28A or Lin28B; or inhibits the expression or activity of a let-7 microRNA, or the composition comprising such agents is an amount that is sufficient to improve organ function by at least 10% (e.g., at least 10%, at least 20%, at least 30%, at least 40%, at least 50%, at least 60%, at least 70%, at least 80%, at least 90%, at least 100, 2-fold, 5-fold, 10-fold, or more). In some embodiments, the organ is kidney. In some embodiments, kidney function is as measured by the glomerular filtration rate (GFR). One skilled in the art (e.g., a clinician) is familiar with methods of evaluating the function of different organs (e.g., brain, intestine, heart, stomach, kidney, and lung).

The agents that increases the expression or activity of Lin28A or Lin28B; or inhibits the expression or activity of a let-7 microRNA, or the composition comprising such agents may be administered repeatedly to a subject (e.g., 2, 3, 4, 5, 6, 7, 8, 9, 10 times or more). In some embodiments, dosage is daily, every other day, every three days, every four days, every five days, or every six days. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the agents used) can vary over time.

In some embodiments, for an adult subject of normal weight, doses ranging from about 0.01 to 1000 mg/kg may be administered. In some embodiments, the dose is between 1 to 200 mg. The particular dosage regimen, i.e., dose, timing and repetition, will depend on the particular subject and that subject's medical history, as well as the properties of the agent (such as the half-life of the agent, and other considerations well known in the art).

For the purpose of the present disclosure, the appropriate dosage of the agents or compositions as described herein will depend on the specific agent (or compositions thereof) employed, the formulation and route of administration, the type and severity of the disorder, previous therapy, the subject's clinical history and response to the agents, and the discretion of the attending physician. Typically the clinician will administer an agent until a dosage is reached that achieves the desired result. Administration of one or more agents can be continuous or intermittent, depending, for example, upon the recipient's physiological condition, and other factors known to skilled practitioners. The administration of an agent may be essentially continuous over a preselected period of time or may be in a series of spaced dose, e.g., either before, during, or after developing a disorder.

In some embodiments, the agent that increases the expression or activity of Lin28A or Lin28B; or inhibits the expression or activity of a let-7 microRNA, or the composition comprising such agents are administered systemically. As such, the agent or composition may be formulated for parenteral administration, e.g., intravenous injection. In some embodiments, the composition comprising the agents that increases the expression or activity of Lin28A or Lin28B; or inhibits the expression or activity of a let-7 microRNA are administered to an organ where organogenesis needs to be prolonged or reactivated (e.g., an organ with reduced function). Direct administration to an organ may be achieved by direct injection. In some embodiments, systemic administration results in a systemic increase in the expression or activity of Lin28A or Lin28B, or systemic inhibition of the expression or activity of a let-7 microRNA. In some embodiments, direct administration of the agent to an organ results in a localized increase in the expression or activity of Lin28A or Lin28B in the organ, or a localized inhibition of the expression or activity of a let-7 microRNA.

A "subject" refers to human and non-human animals, such as apes, monkeys, horses, cattle, sheep, goats, dogs, cats, rabbits, guinea pigs, rats, and mice. In one embodiment, the subject is human. In some embodiments, the subject is an experimental animal or animal substitute as a disease model. A "subject in need thereof" refers to a subject who has or is at risk of reduced organ (e.g., brain, intestine, heart, stomach, kidney, or lung) function due to any factor. Factors that may cause reduced organ function include, without limitation, premature birth, malnutrition, disease, trauma, or surgical ablation.

In some embodiments, the subject is a human infant. A "human infant" refers to a human from about the age of 4 weeks of age to about 3 years of age. In some embodiments, the subject is born prematurely. "Born prematurely" refers to birth (or delivery) that occurs before a normal gestational term for a given species. In humans, a full gestational term is about 40 weeks and may range from 37 weeks to more than 40 weeks. Low gestational age, in humans, akin to a premature birth is defined as birth that occurs before 37 weeks of gestation. As such, the subjects of the present disclosure, in some embodiments, are born before 37 weeks of gestation, including those born at even shorter gestational terms (e.g., before 36, before 35, before 34, before 33, before 32, before 31, before 30, before 29, before 28, before 27, before 26, before 25, before 24, before 23, before 22, before 21, before 20, before 19, before 18, before 17, before 16 or before 15 weeks of gestation).

In some embodiments, the subject of the present disclosure suffers from intrauterine growth restriction. A subject that suffers from "intrauterine growth restriction" refers to a subject (e.g., a fetus) whose estimated weight is below the 10th percentile for its gestational age and whose abdominal circumference is below the 2.5th percentile. Intrauterine growth restriction carries an increased risk of perinatal mortality and morbidity.

In some embodiments, the subject is a malnourished subject (e.g., a malnourished fetus). A malnourished fetus refers to a fetus suffering from malnutrition due to poor maternal diet (lacking proper nutrients) during pregnancy. Maternal malnutrition increases the risk of poor pregnancy outcomes including premature or low-birth-weight infants.

Some of the embodiments, advantages, features, and uses of the technology disclosed herein will be more fully understood from the Examples below. The Examples are intended to illustrate some of the benefits of the present disclosure and to describe particular embodiments, but are not intended to exemplify the full scope of the disclosure and, accordingly, do not limit the scope of the disclosure.

EXAMPLES

Example 1

Babies delivered prematurely face overwhelming difficulties. Premature births are associated with many major complications mostly at birth, but also throughout maturity including infection, acute intestinal inflammation, acute and chronic lung disease, and low nephron endowment. Infants born too early are almost always placed on the steroid, dexamethasone to speed up the process of lung and kidney development, which leads to a host of side effects. Kidney disease represents a major public health issue in large part because nephrons, which are responsible for the filtration function of the kidney, form only during development in utero, and reach completion at approximately 34-36 weeks of gestation. Therefore, children who are born prematurely or suffer from malnutrition, disease, trauma, or surgical ablation have a reduced number of nephrons, or "nephron endowment." Because new nephrons never form postnatally, children with a compromised nephron endowment are at increased risk of hypertension and development of cardiovascular and renal diseases as well as insulin resistance and Type 2 diabetes in later life[11-13]. Several studies have attempted to emulate nephron formation in vitro by the directed differentiation of pluripotent stem cells towards renal progenitor fate[14-16]. However, anatomically complicated organs like the kidney are particularly challenging for stem cell-based therapies[17].

It is reported herein that Lin28A and Lin28B are expressed in early brain, intestine, heart, stomach, kidney, and lung, with their expression decreasing throughout development as previously noted for other organs (with the exception of Lin28A in the lung). Absolute quantification of mRNA together with immunoblots for protein expression, indicated that Lin28B has prolonged and higher expression than Lin28A in both organs. Analysis of all the mature let-7 family members indicated that their expression is also similar in both kidney and lung, showing low to no expression early-mid gestation, increasing mid-late gestation into adulthood. This conclusively demonstrates the Lin28/let-7 axis is conserved. Next, the transient extension of Lin28B expression from E16.5 to P5 in embryonic kidneys led to prolonged nephrogenesis is demonstrated. Interestingly, not only are a pool of progenitors expanded, but these cells properly differentiate into functional glomeruli (the structural and functional units of the kidney). As a result, kidney function is increased over control as measured by their filtration rate (GFR) and creatinine (byproduct of protein degradation) levels. Several Let-7 family members are transcribed as clusters. A whole body knockout of the highest expressed precursor cluster in mice was examined. Knockout of cluster a, f, and d located on mouse chromosome 13, led to prolonged nephrogenesis and more functional glomeruli measured by their GFR and creatinine similar to what was observed in the Lin28B overexpression mouse model. Genetic manipulation of the Lin28/let-7 axis revealed the enormous potential for therapeutic intervention. Next, let-7 in wild type mice was pharmacologically inhibited using antagomirs. Antagomirs are chemically engineered oligonucleotides that are efficient and specific silencers of endogenous microRNAs. Using an ex vivo organ culture of kidneys a statistically significant increase in progenitors marked by Eya1 and Six2 was demonstrated. To take the therapeutics to the next level, fluorescently labeled antagomirs were administered in utero and it was found that several major organs such as heart, lung, intestines, brain, and kidney are able to uptake the antagomir against let-7a. The project outlined herein envisions a new strategy to prolong or reactivate the period of nephrogenesis in newborns and holds great promise for children suffering from the complications of premature birth and/or intrauterine growth restriction.

Figure 1B:
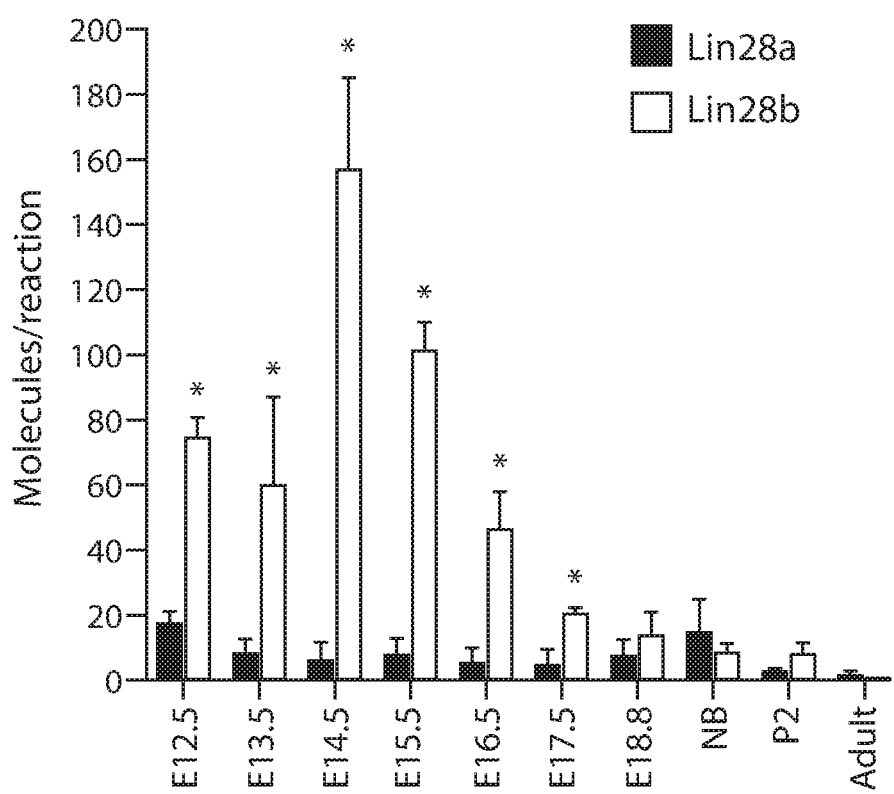

Endogenous Lin28A and Lin28B expression in wild-type embryonic kidneys and other organs was measured. It was discovered that Lin28B is expressed at high levels in the early embryonic kidney followed by a rapid decline after embryonic day 15.5 (E15.5), which is the time when the first functional nephrons are formed in kidney development. The expression of Lin28B around the middle of gestation when new nephrons are forming suggests the protein plays an important role in nephrogenesis. In addition, this confirmed the previously established observation that Lin28A is not expressed until E13.5, after which expression wanes (FIG. 1A; Urbach, Yermalovich, et al., Genes and Development, 2014). Interestingly, when the absolute expression of Lin28A and Lin28B was measured it was found that the amount of Lin28B mRNA is ten-fold higher compared to Lin28A in early kidney development (FIG. 1B). The high and prolonged expression of Lin28B suggests that this protein plays a more dominant role in nephrogenesis than Lin28A.

Figure 3A:
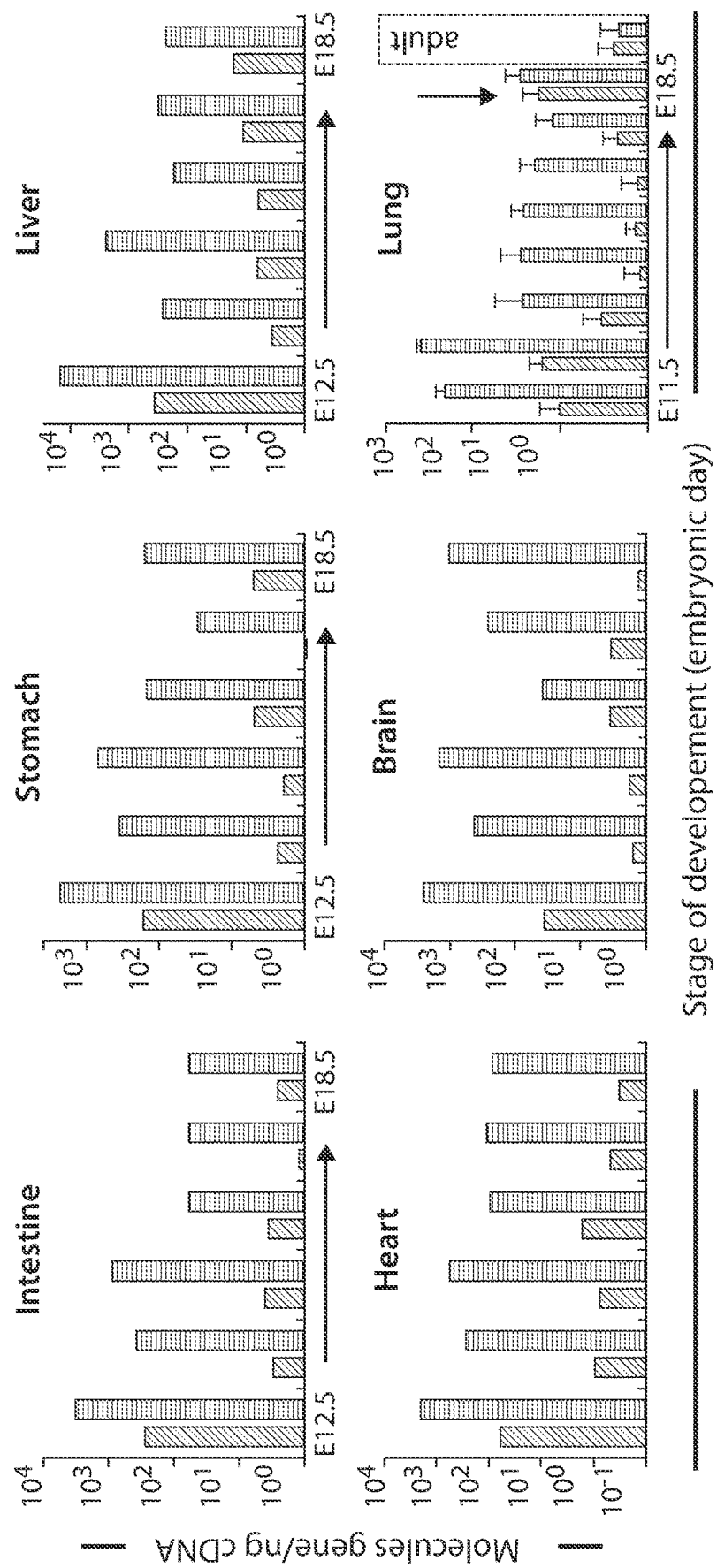
FIGS. 3A to 3C. Analysis of endogenous expression of Lin28 in mouse embryonic organs.
Figure 3B:
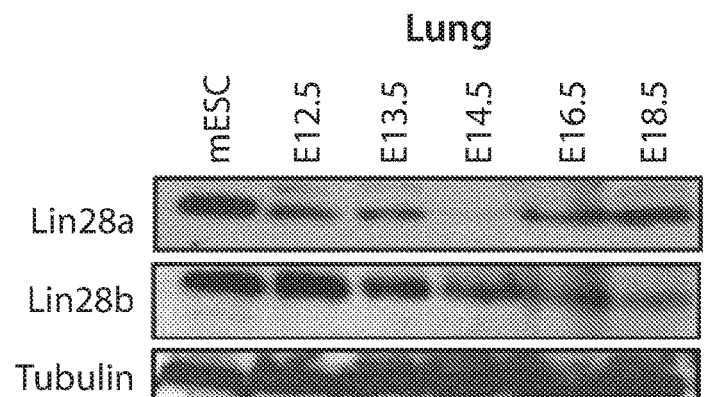
Figure 3C:
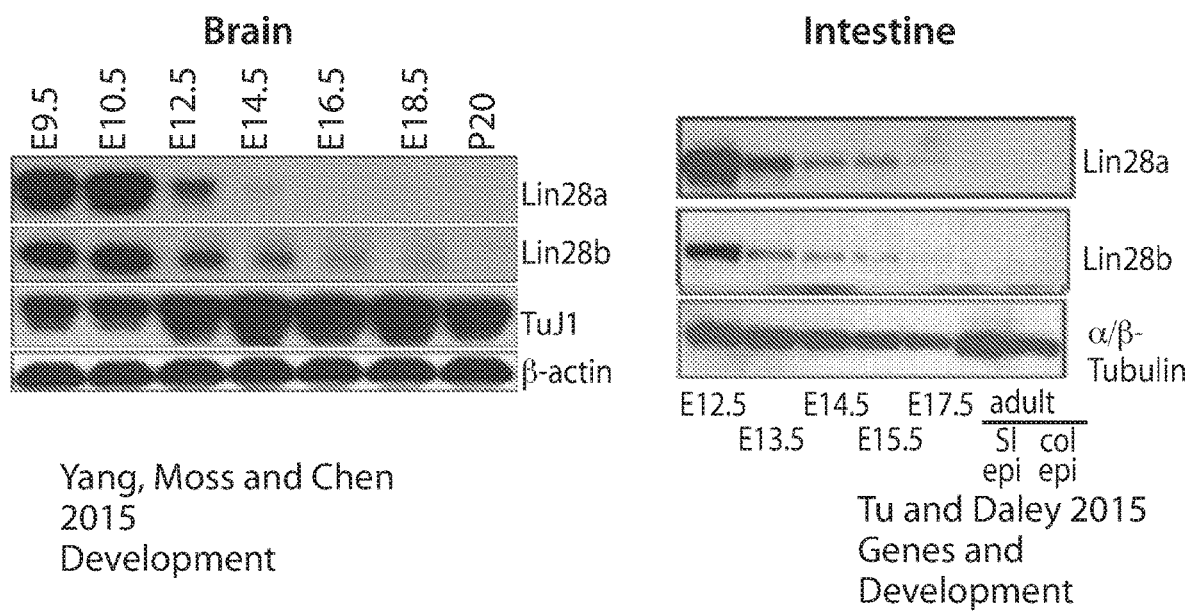

The expression dynamics of Lin28A and Lin28B in other organs are similar to kidney. Lin28A and Lin28B are expressed in early brain, intestine, heart, stomach, and lung, with their expression decreasing throughout development (with the exception of Lin28A in the lung) (FIGS. 3A-3C). The absolute quantification of mRNA together with immunoblots for protein expression in lung, indicated that Lin28B has prolonged and higher expressed than Lin28A similarly to kidney.

Figure 1C:
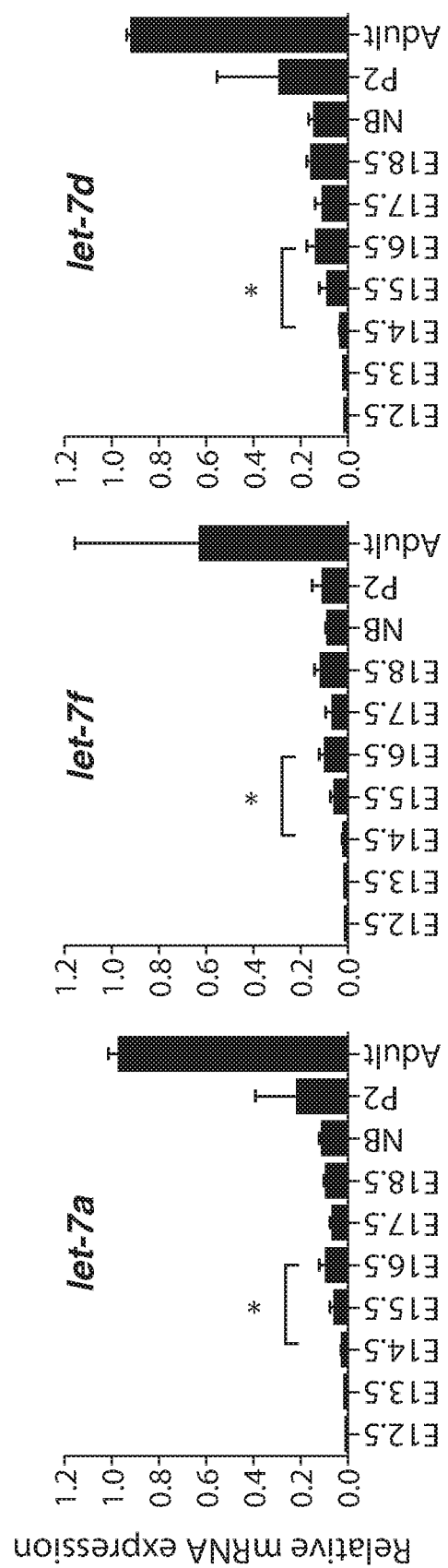
Figure 1D:
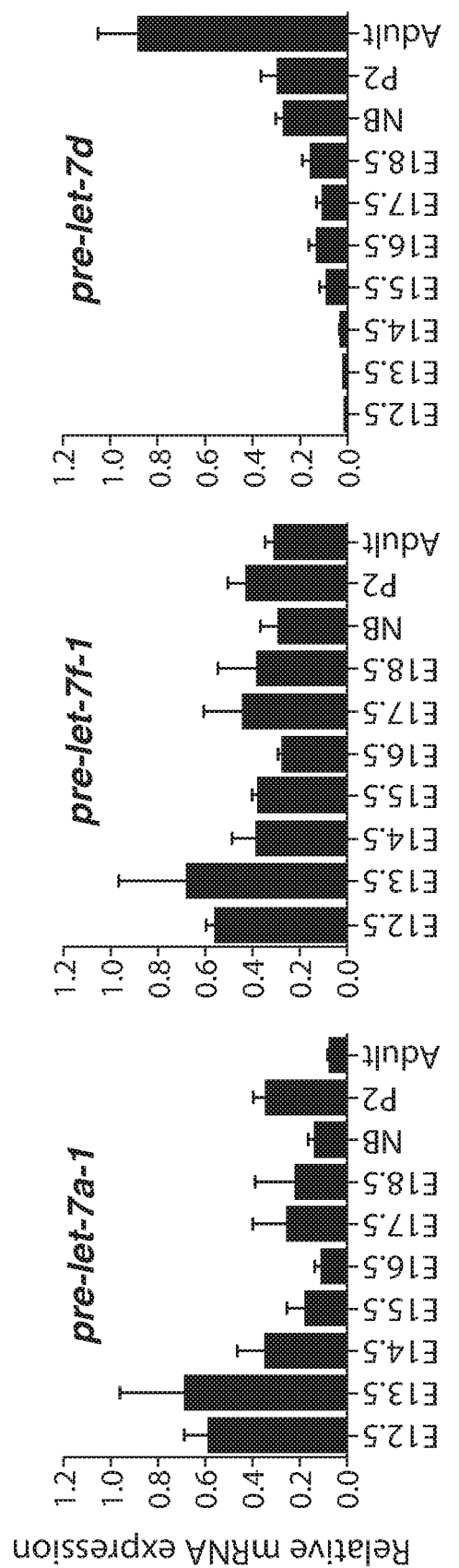
Figure 2A:
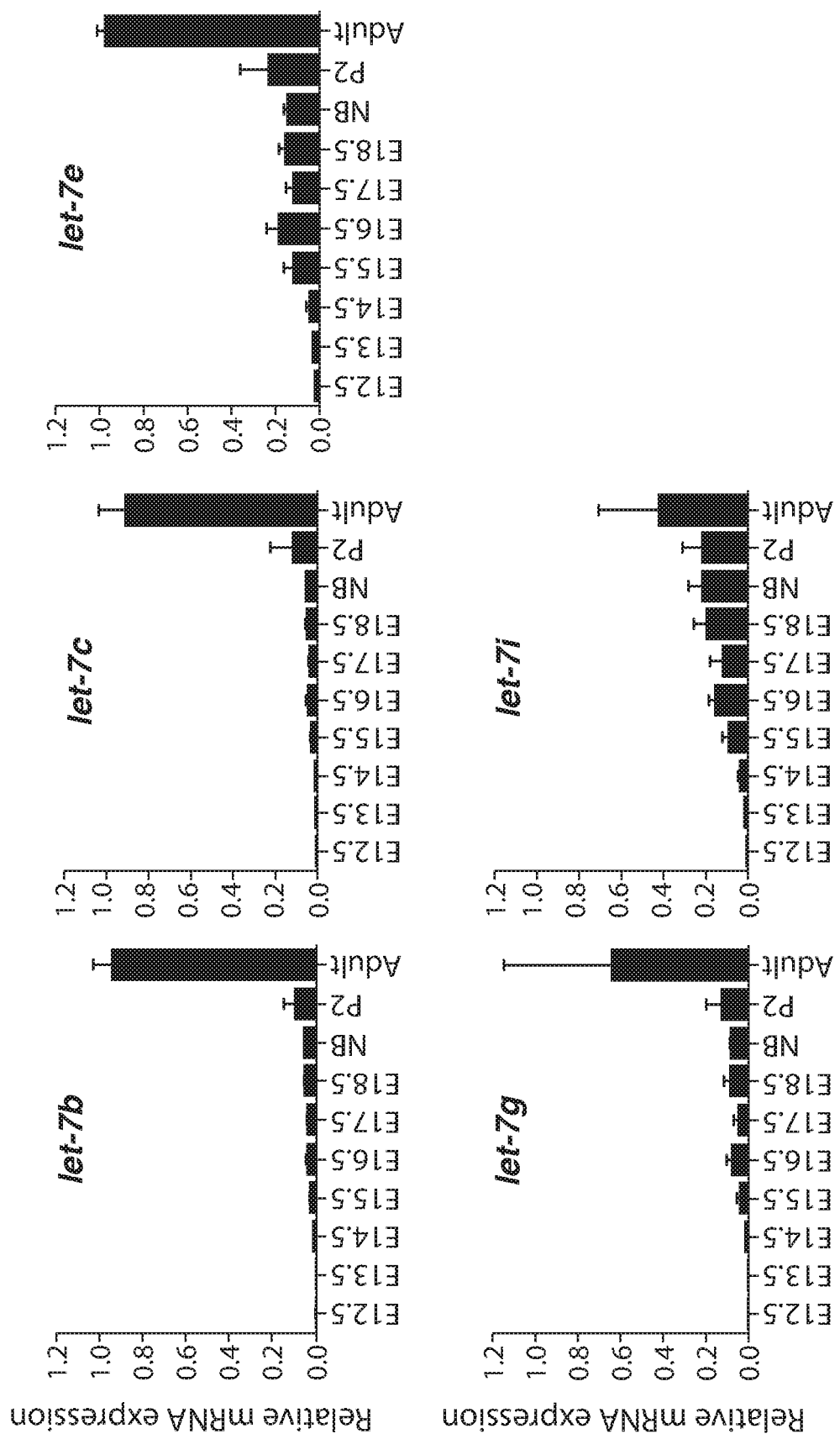
FIGS. 2A to 2B. Analysis of endogenous expression of mature and precursor let-7 in mouse embryonic kidney.
Figure 2B:
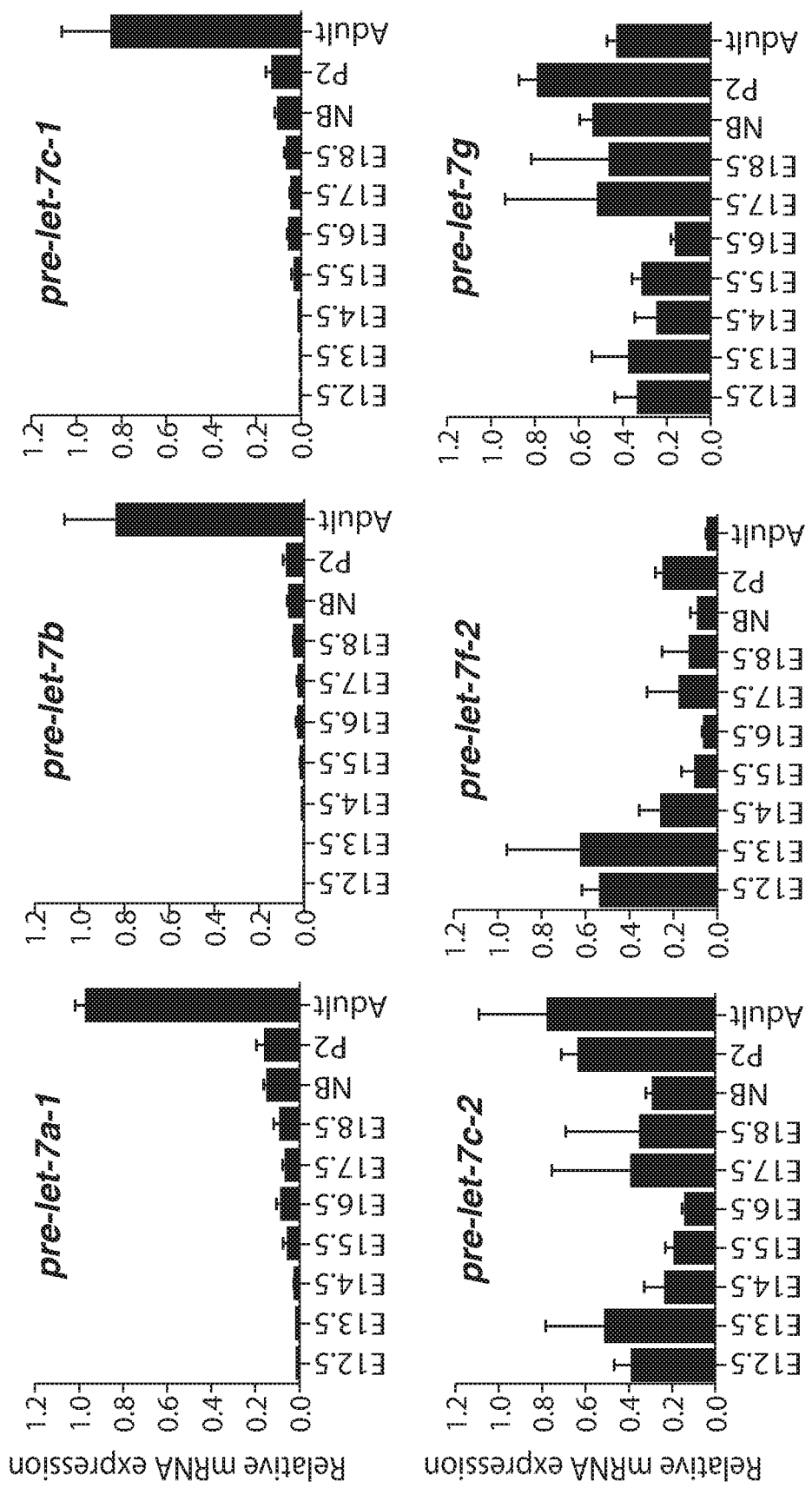
Figure 2B:
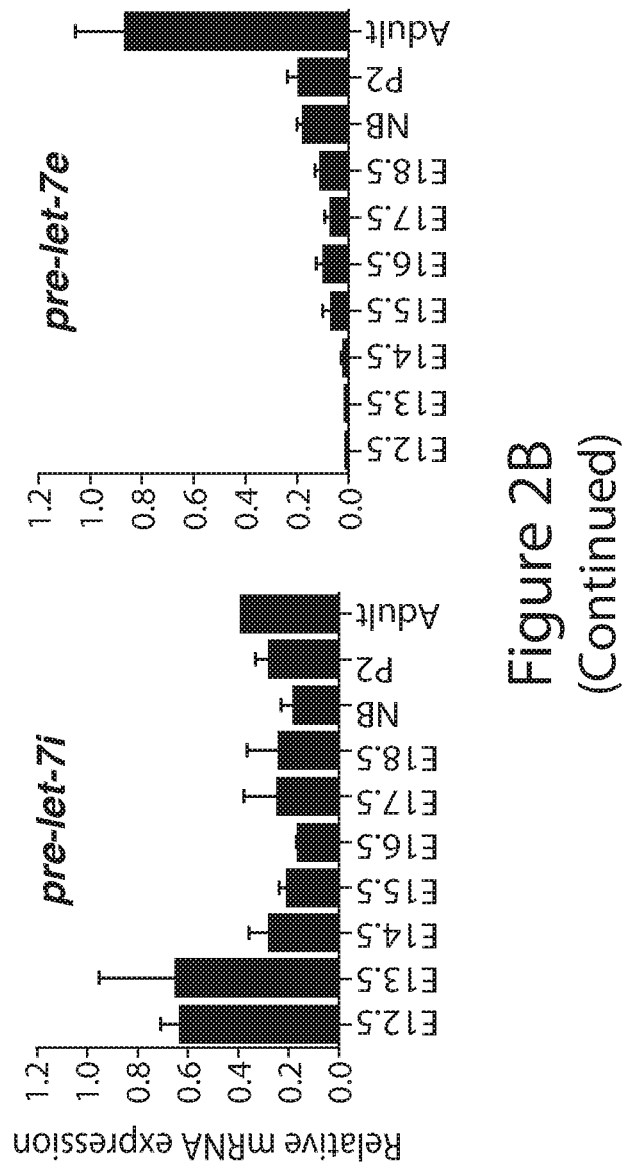

Next, let-7 levels during nephrogenesis in wild-type embryonic kidneys and lungs were analyzed. It was found that expression of mature let-7 microRNAs negatively correlates with expression of Lin28B during kidney development and all eight let-7 family members follow a similar pattern of very low levels of expression until E14.5, followed by two- to three-fold increase in their expression beginning E15.5 (FIG. 1C and FIG. 2A). To determine whether let-7 microRNAs are suppressed during early nephrogenesis due to the presence of Lin28A and/or Lin28B, the expression of the let-7 precursor microRNAs were measured. Interestingly, while one group of precursors, pre-let7-a2, pre-let7-b1, pre-let7-c1, pre-let7-d1, pre-let7-e1, have the same pattern of expression as their mature family members (FIG. 1D and FIG. 2B), a second group, pre-let7-a1, pre-let7 f1, pre-let7 f2, pre-let7-g1, pre-let7-i1, is up-regulated during early nephrogenesis until E15.5 (FIG. 1D and FIG. 2B), These data suggest that Lin28B likely contributes to early kidney development by suppression of the latter group of precursor microRNAs.

Figure 4:
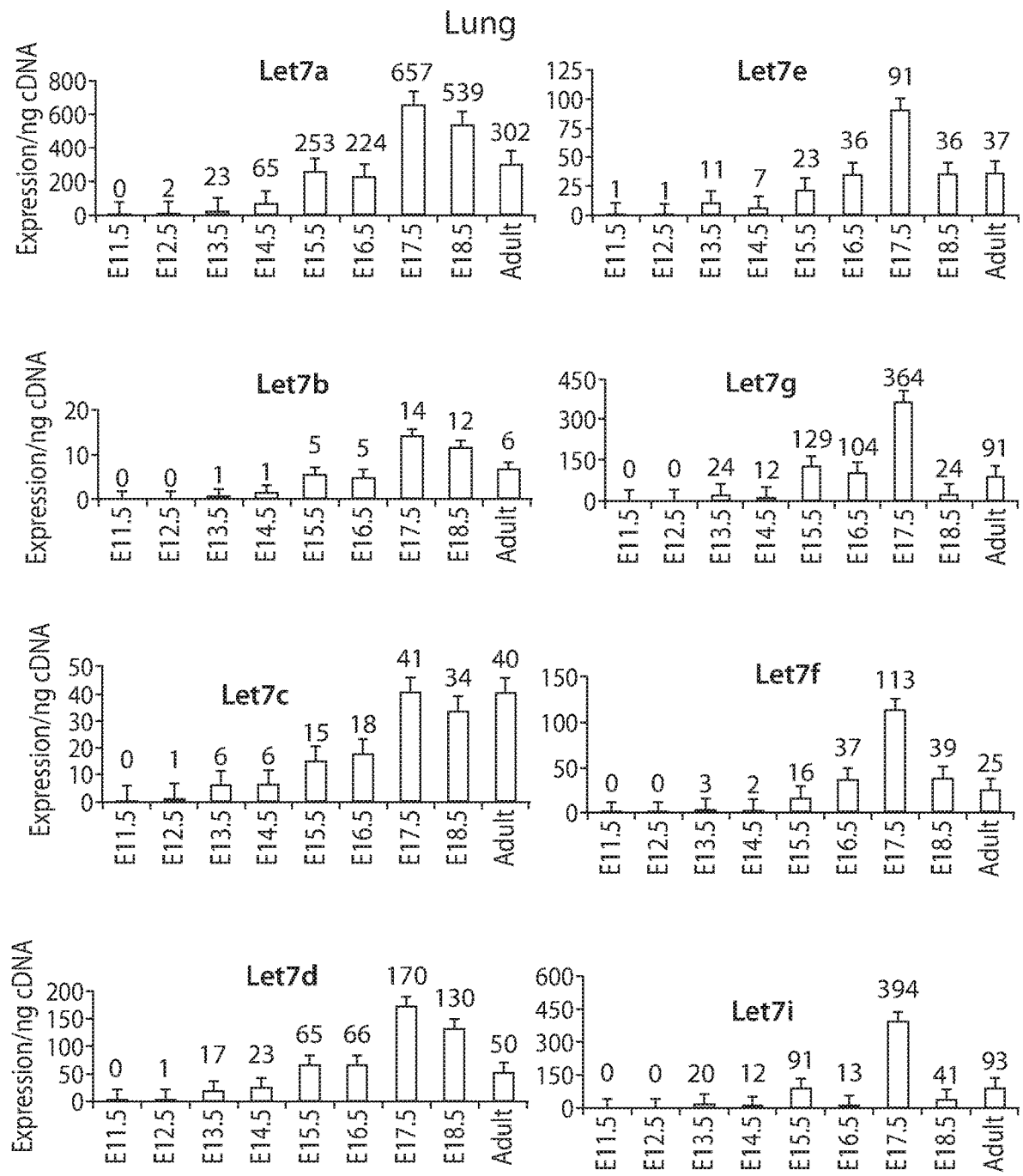
FIG. 4. Analysis of endogenous expression of Let7 family members in mouse embryonic lung. Graphs of absolute expression of all let7 family members using standards.

Analysis of all the mature Let-7 family members in lung, similarly to kidney, showed low to no expression early-mid gestation, increasing mid-late gestation into adulthood (FIG. 4). This conclusively demonstrates the Lin28/let-7 axis is conserved.

Figure 5A:
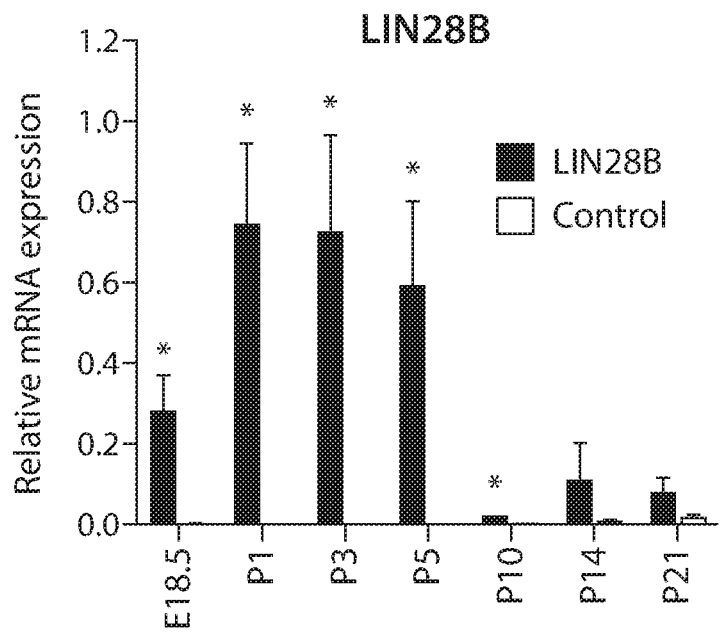
FIGS. 5A to 5G. Transient overexpression of LIN28B in embryonic kidney at the end of gestation prolongs the period of nephrogenesis.
Figure 5B:
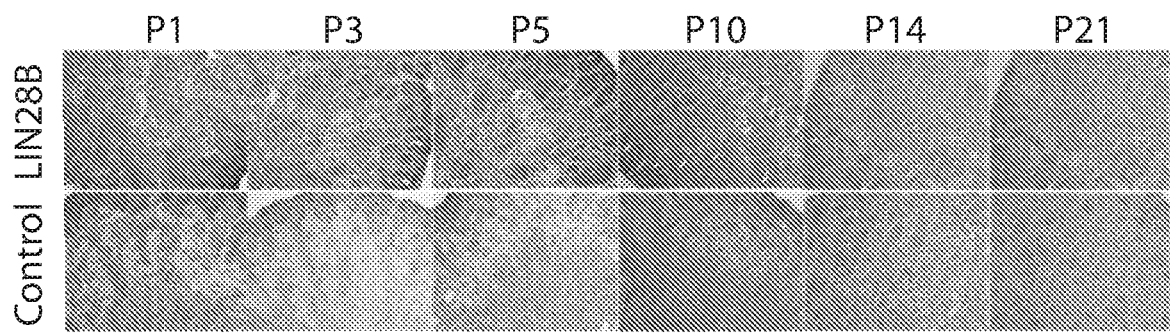
Figure 5C:
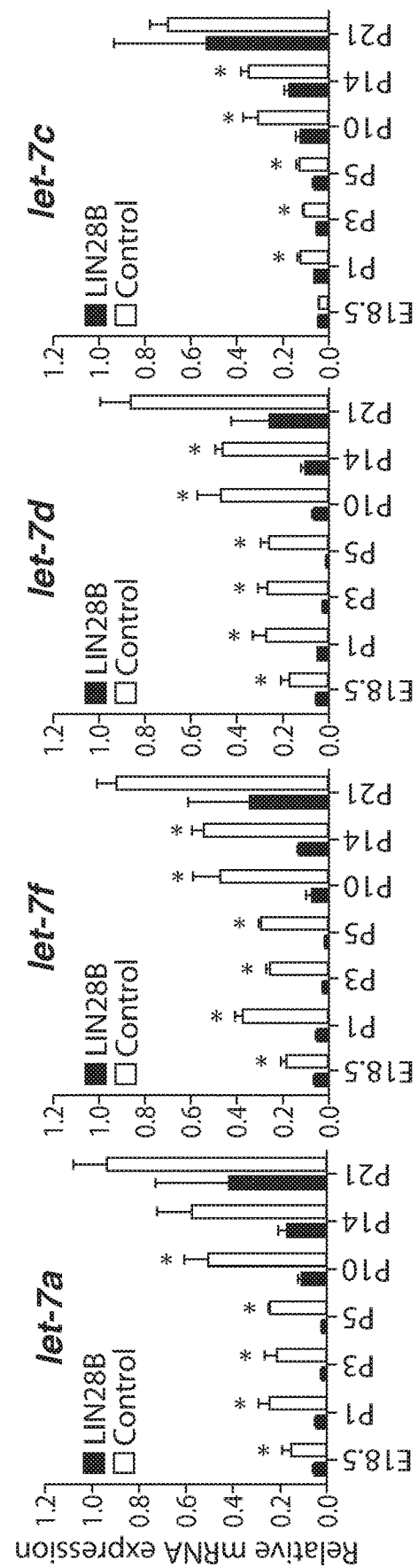
Figure 5D:
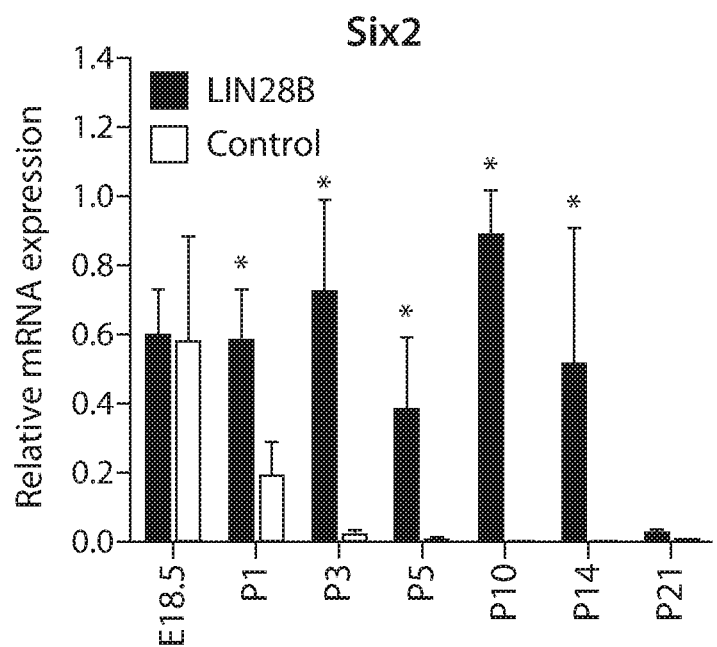
Figure 5E:
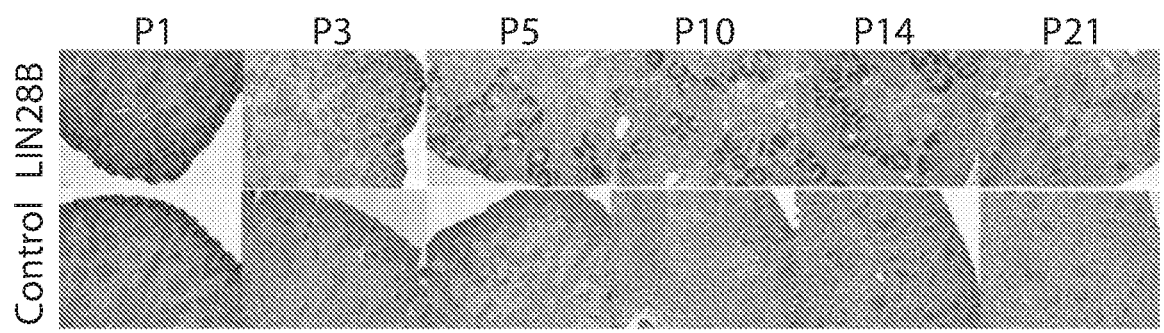
Figure 5F:
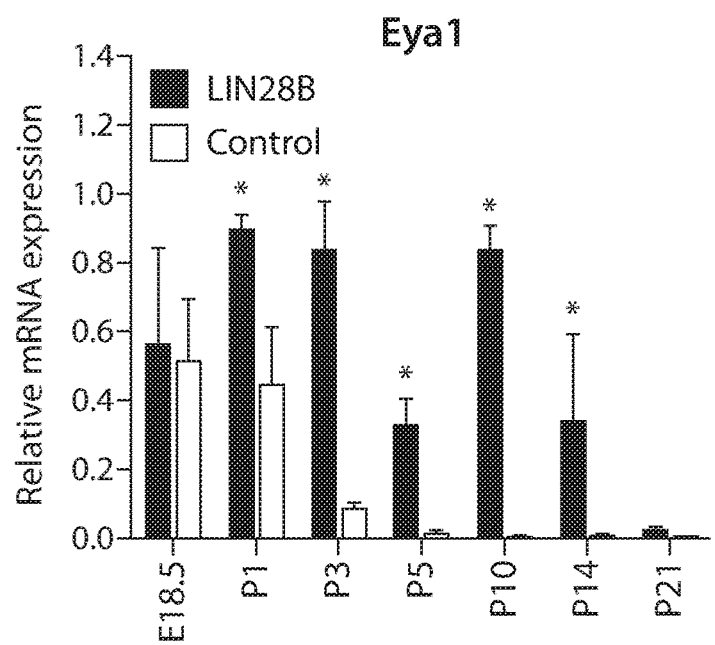
Figure 5G:
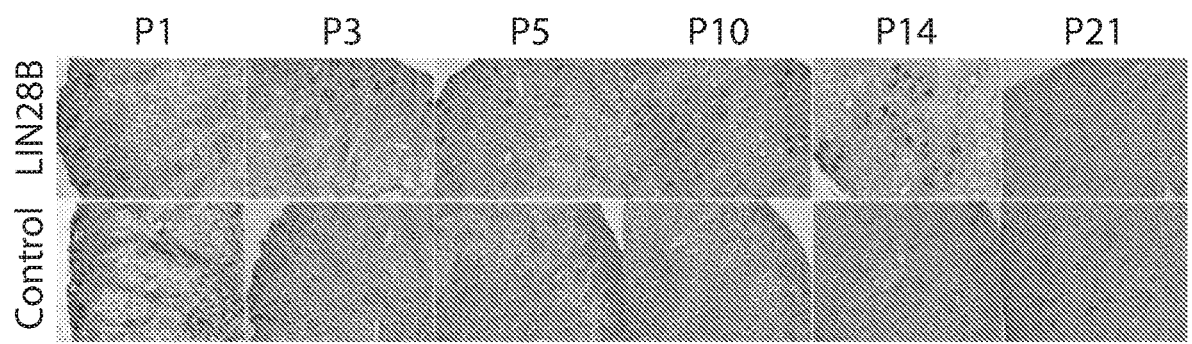
Figure 6A:
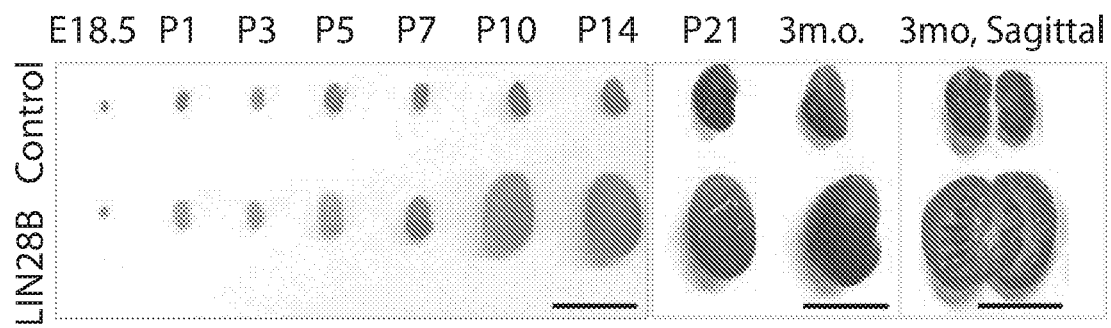
FIGS. 6A to 6I. LIN28B transient overexpression enhances renal function.
Figure 6B:
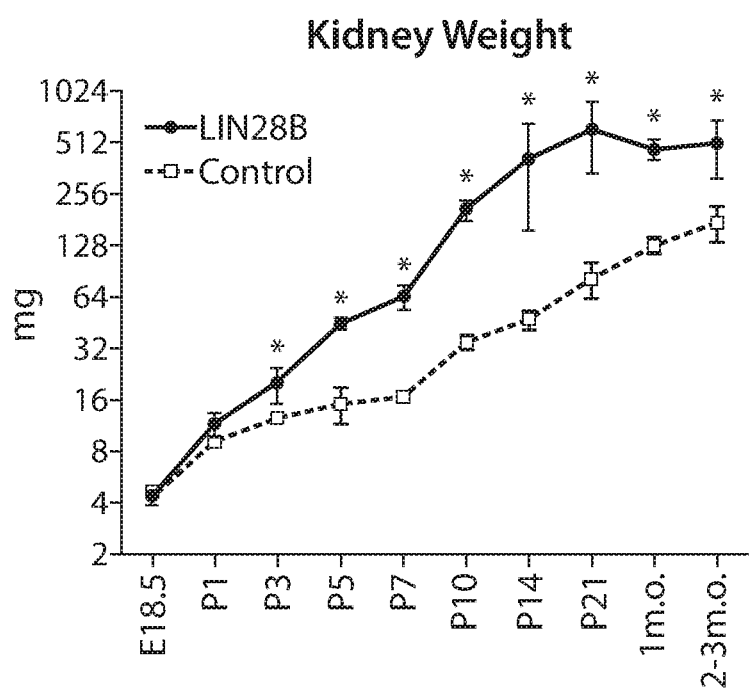
Figure 6C:
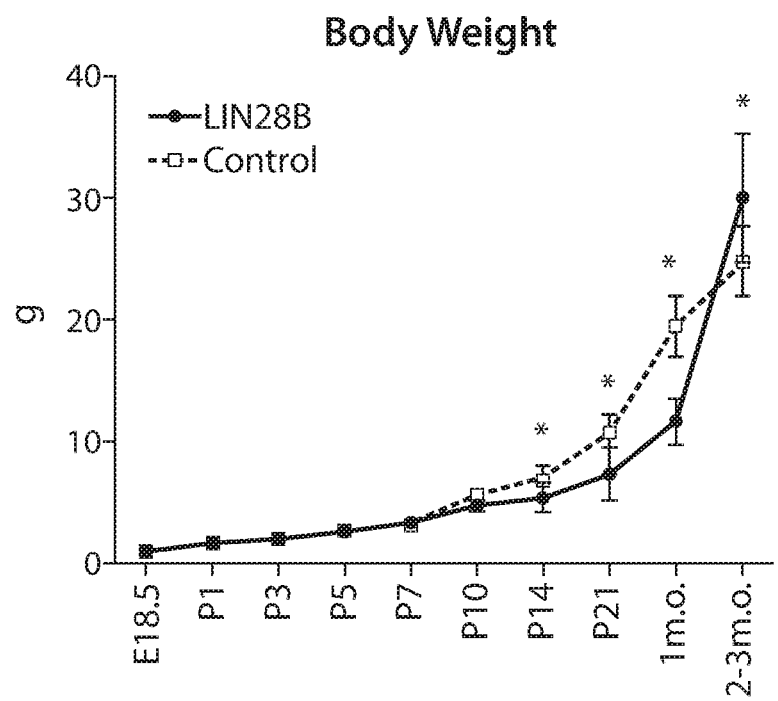
Figure 6D:
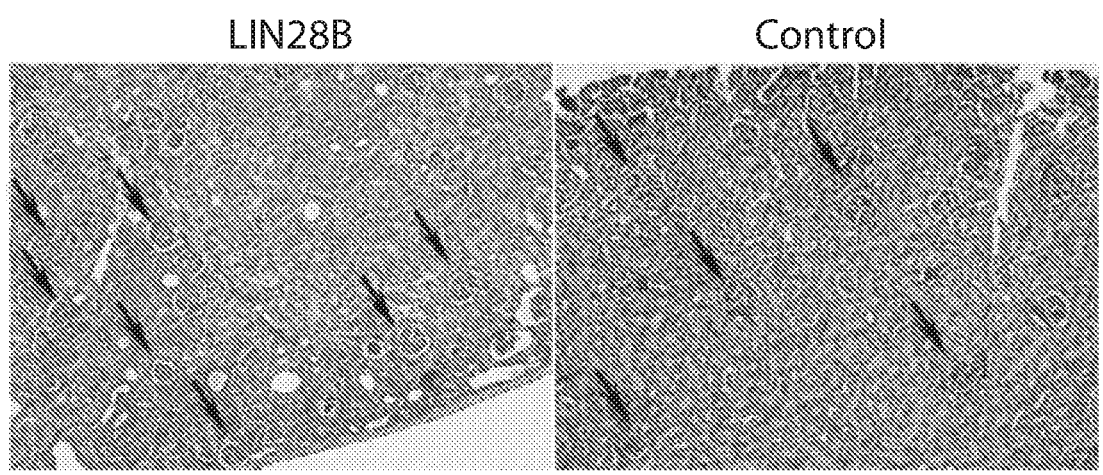
Figure 6E:
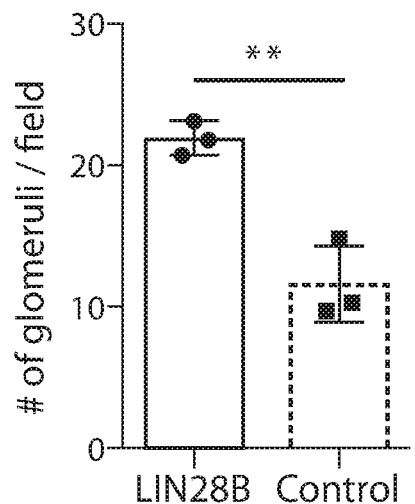
Figure 6F:
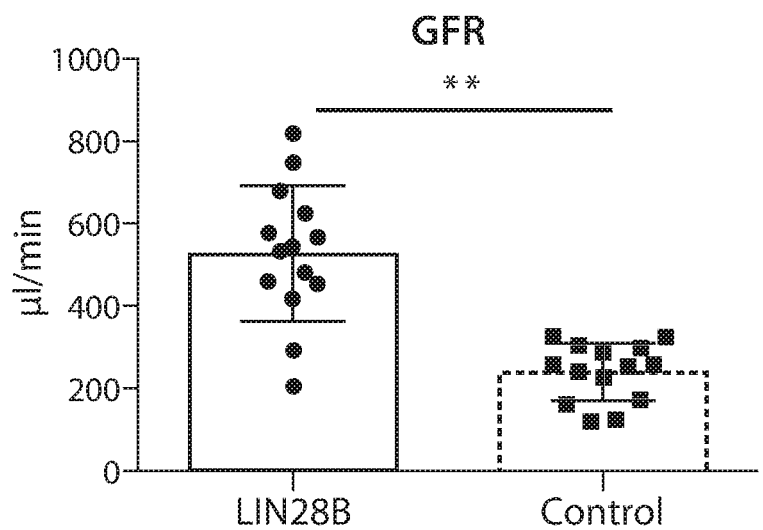
Figure 6G:
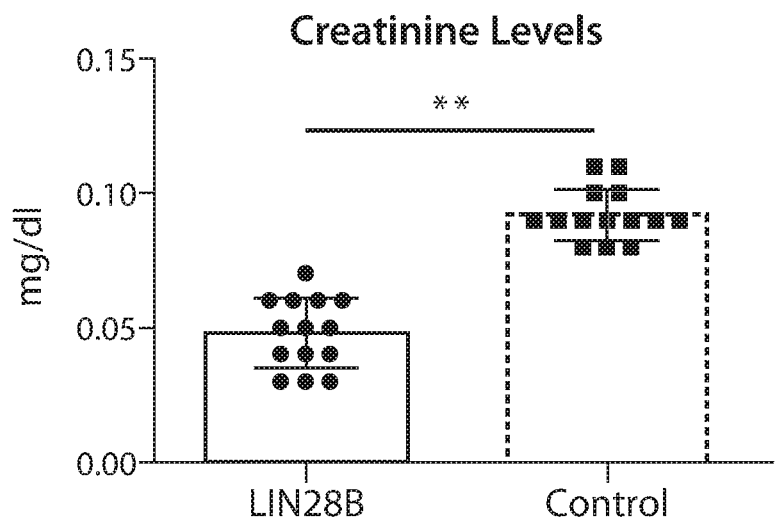

Optimized conditions to prolong Lin28B expression in embryonic kidneys led to prolonged nephrogenesis. To extend Lin28B expression in embryonic kidneys, LIN28B was transiently overexpressed using the Wt1-Cre; Lox-STOP-Lox-rtTA-LIN28B transgenic mouse model. Transient overexpression of LIN28B for 7 days from E16.5 to P5 (FIGS. 5A and 5B) resulted in suppression of all let-7 microRNAs (FIG. 5C), and extended expression of kidney progenitor cells as measured by as measured by immunohistochemistry and qPCR using Six2, a kidney progenitor, and Lef1, renal vesicles markers (FIGS. 5D-5G). LIN28B transgenic mice had significantly larger kidneys as measured by both size and weight (FIGS. 6A and 6B) and these kidneys demonstrated a statistically significant increase in glomeruli count, filtration rate, and creatinine levels relative to controls (FIGS. 6D-6G). The body weight of the LIN28N transgenic mice and the control mice are comparable (FIG. 6C). These findings indicate that prolonged LIN28B expression during kidney development can effectively extend the period of nephrogenesis, leading to increased kidney function.

Figure 6H:
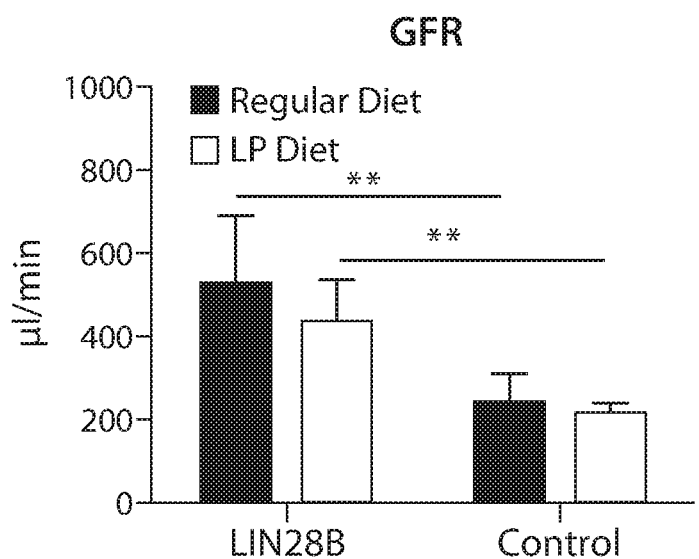
Figure 6I:
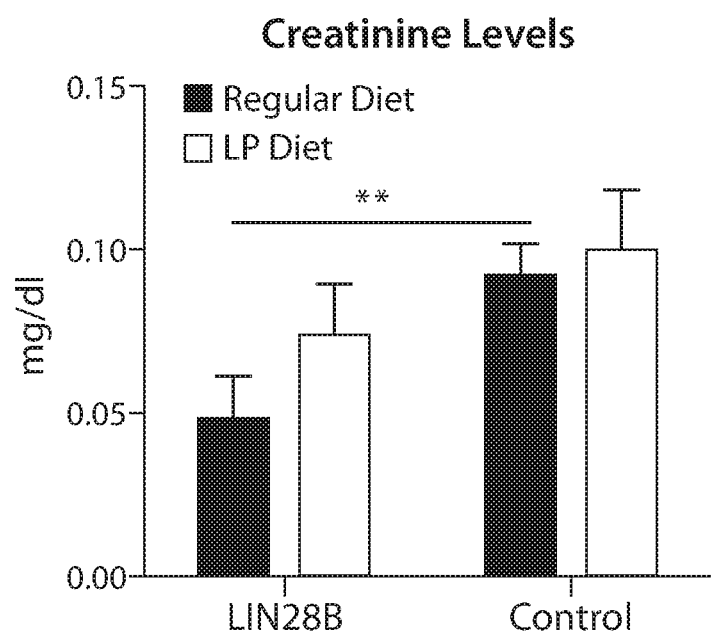
Figure 7A:
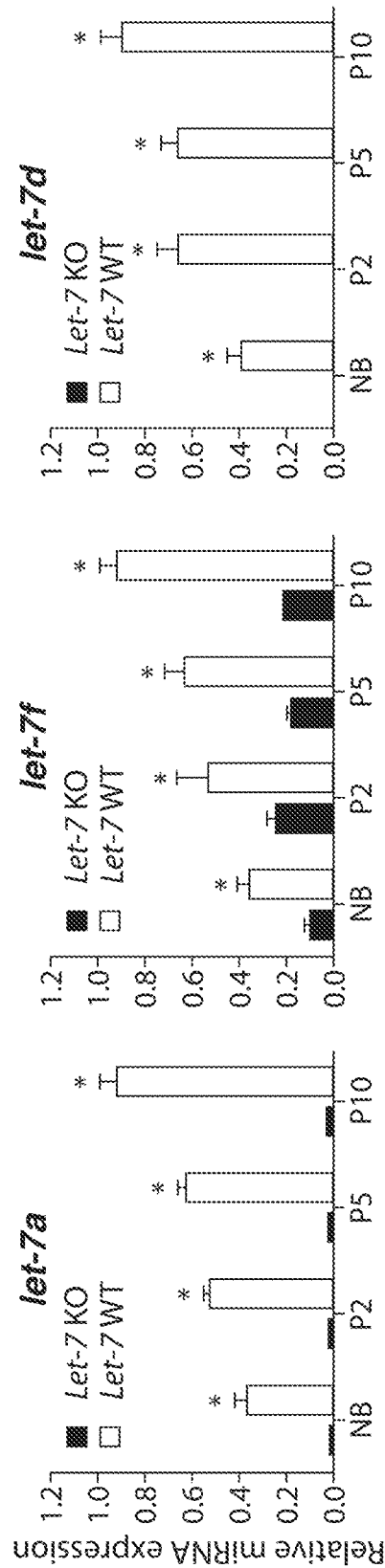
FIGS. 7A to 7L. Lin28B regulates nephrogenesis in a let-7 dependent manner.
Figure 7B:
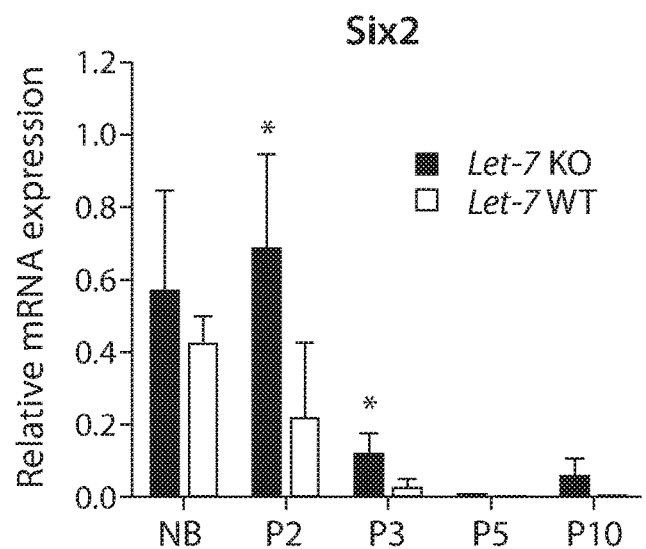
Figure 7C:
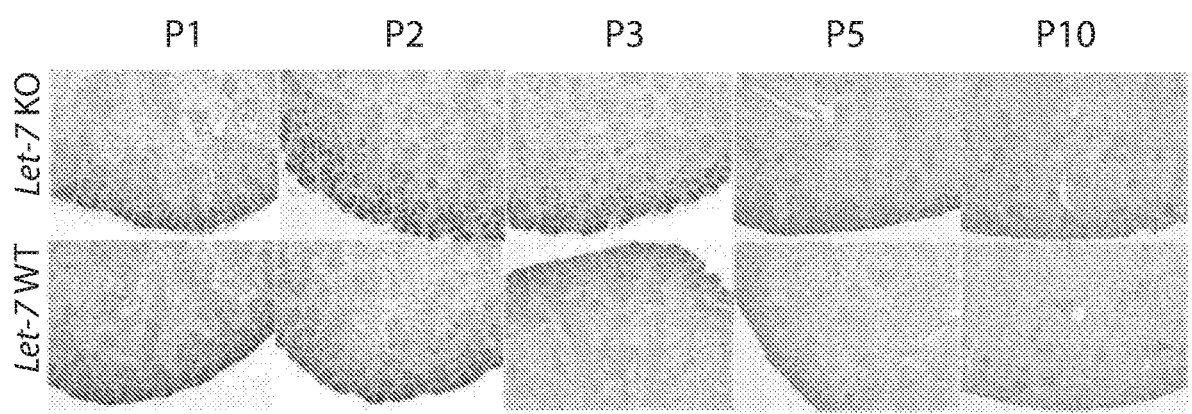
Figure 7D:
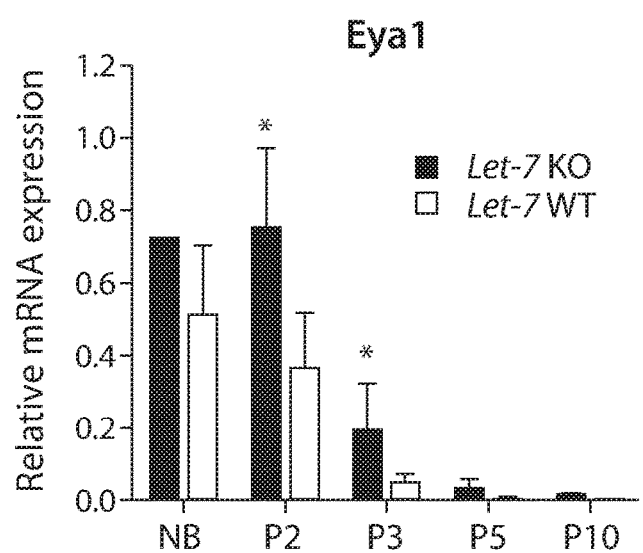
Figure 7E:
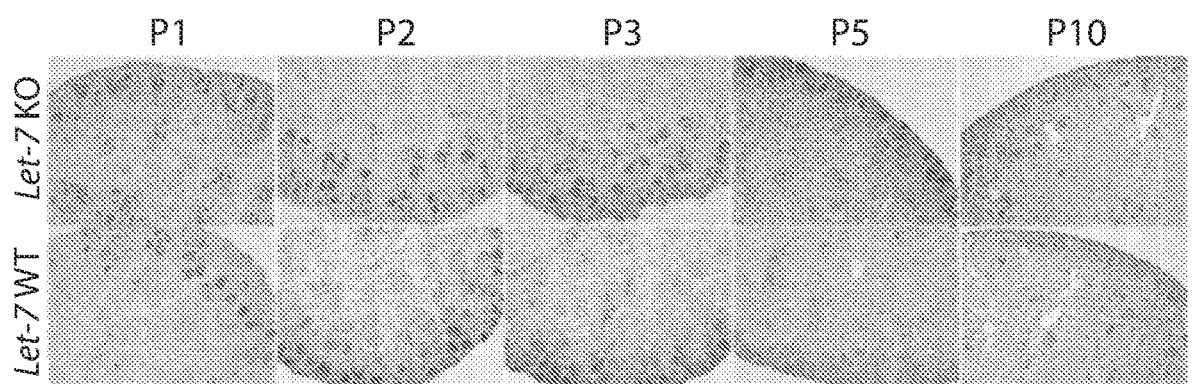
Figure 7F:
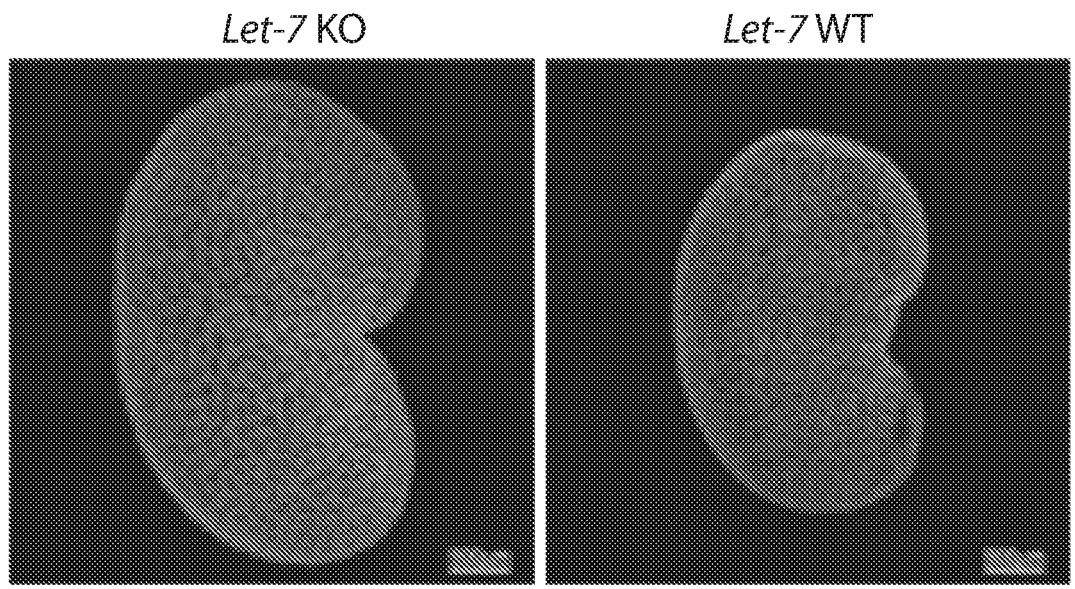
Figure 7G:
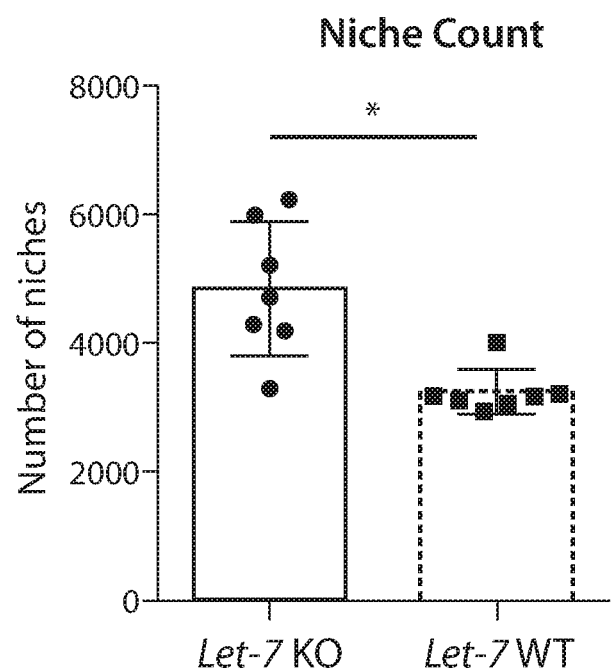
Figure 7H:
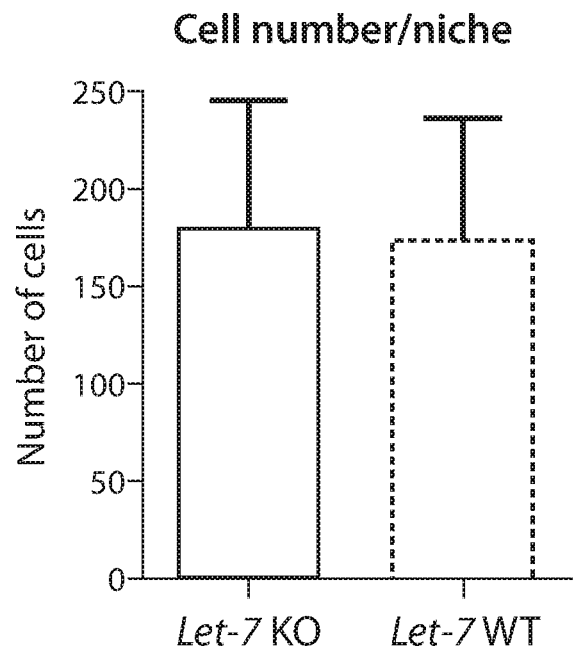
Figure 7I:
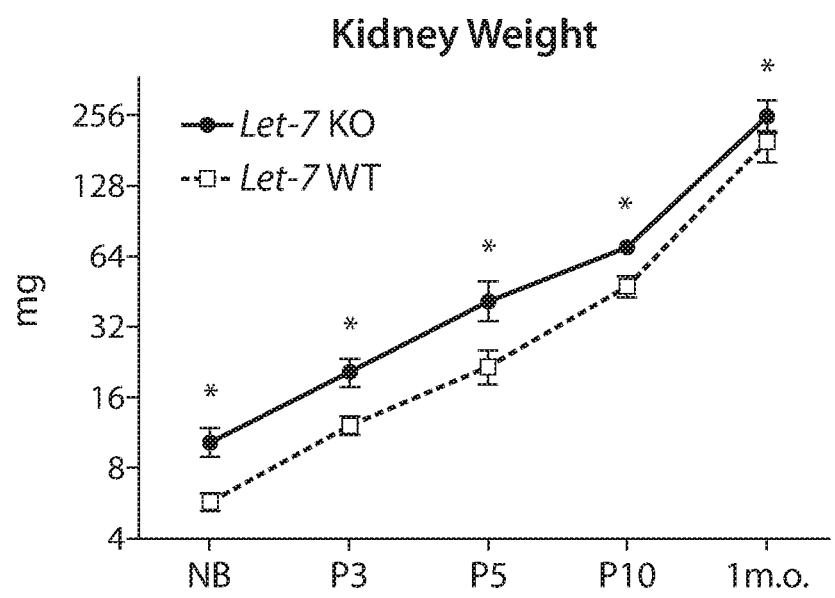
Figure 7J:
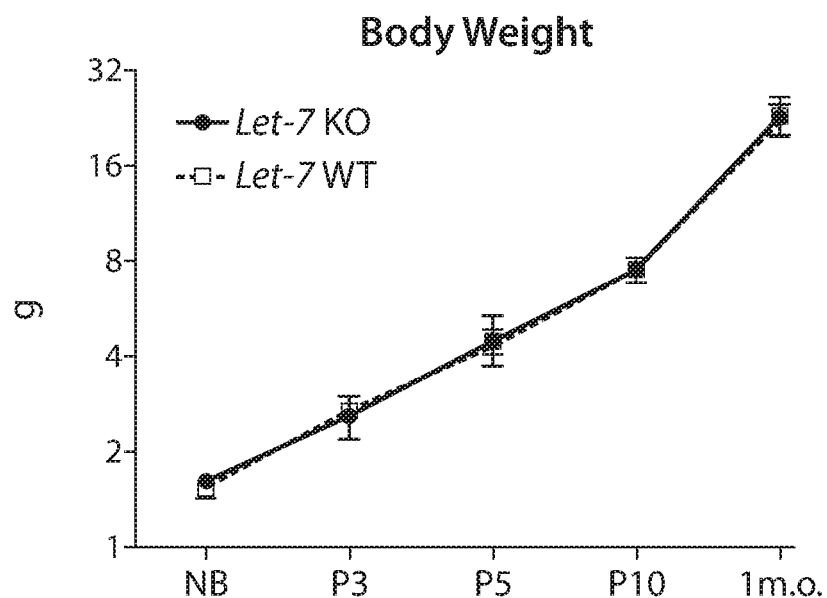
Figure 7K:
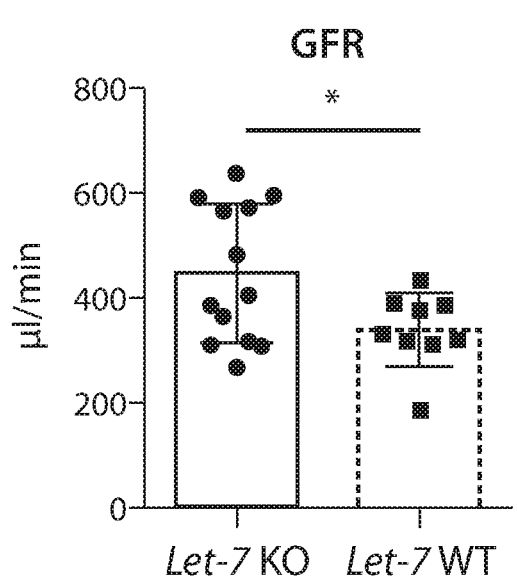
Figure 7L:
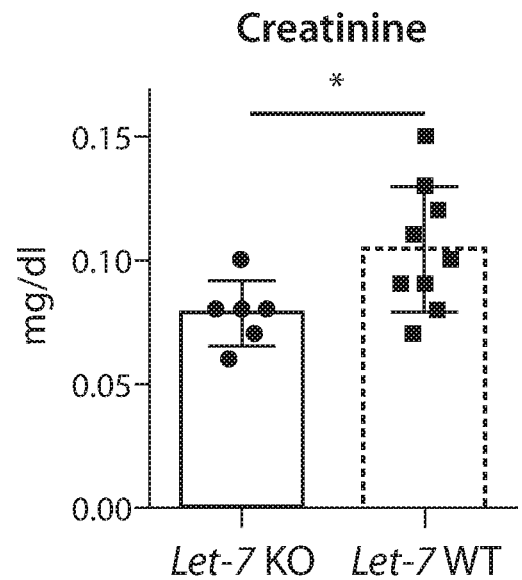

Next, low-nephron endowment rescue was studied. The aim was to determine whether enforced transient expression of Lin28B in embryonic kidney can rescue the effects of malnutrition on nephron endowment in vivo. A nutritionally poor maternal diet can reduce nephron endowment in the offspring[18,19]. To test whether enforced expression of Lin28B in neonates can rescue effects of malnutrition on nephron endowment, Lin28B transgenic mice were protein-restricted (9% casein-diet) throughout pregnancy and as a result the offspring of these animals had reduction in kidney function as measured by GFR and Creatinine levels compared to offspring of mothers on a normal diet (24% casein) (FIGS. 6H and 6I). Lin28B prolongs the period of nephrogenesis in a let-7 dependent manner. To test whether enforced expression of Lin28B in developing kidney prolongs the period of nephrogenesis in a let-7 dependent manner, analyzed constitutive let-7 (let-7a-1, let-7f-1, let-7d) cluster KO mouse model (FIG. 7A). Similarly to Lin28B transgenic mice let-7 cluster KO mice extend the expression of kidney progenitor cells as measured by immunohistochemistry and qPCR using Six2, a kidney progenitor, and Lef1, renal vesicles markers (FIGS. 7B-7E). In addition, let-7 cluster KO kidneys have significantly larger kidneys as measured by both size and weight (FIG. 7I) and these kidneys demonstrated a statistically significant increase in niche count (FIGS. 7F and 7G), filtration rate, and creatinine levels relative to controls (FIGS. 7K and 7L). These findings indicate that Lin28B prolongs the period of nephrogenesis in a let-7 dependent manner.

Figure 8:
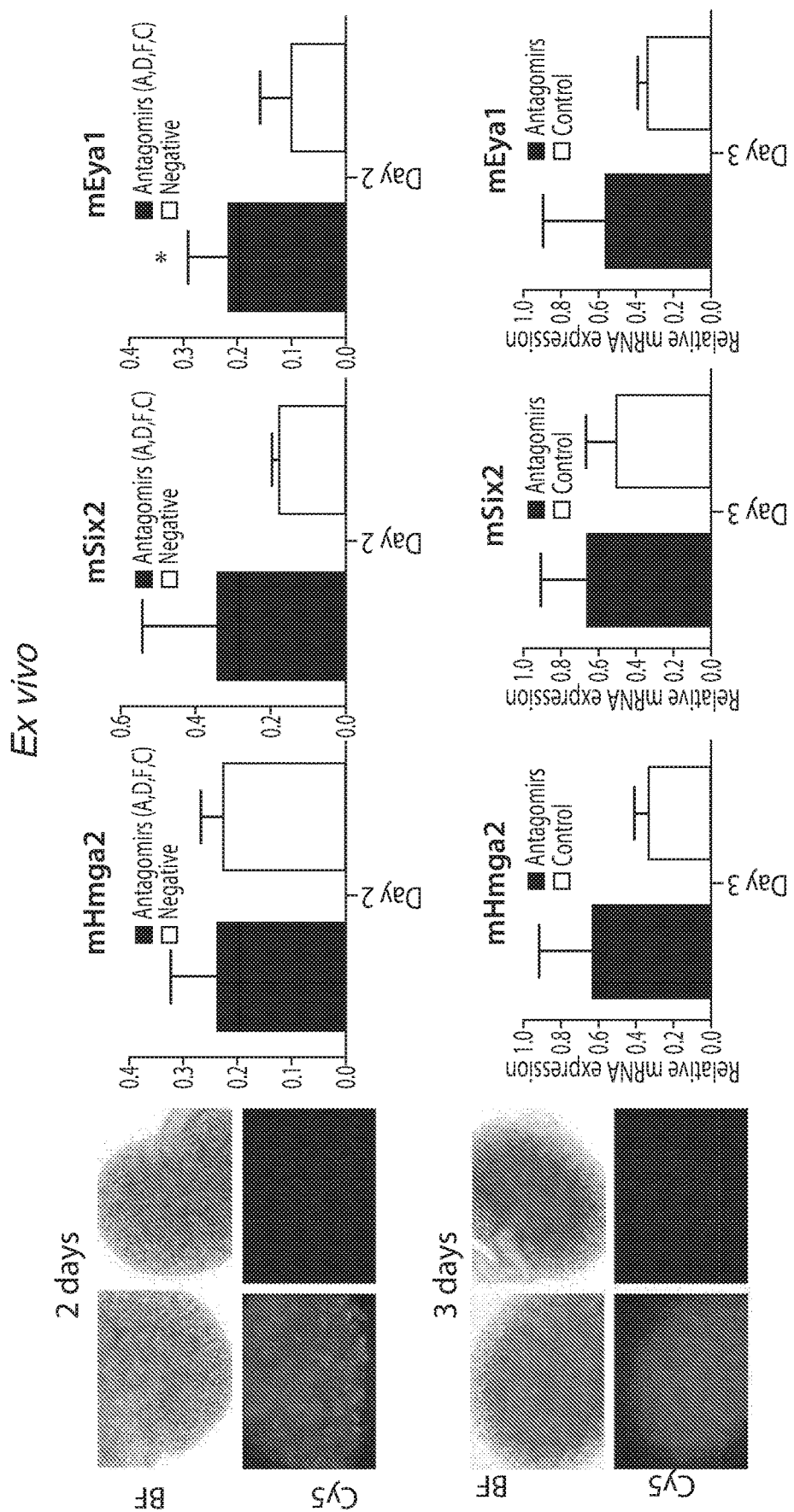
FIG. 8. Antagomirs ex vivo. Ex vivo: Kidney organ culture for 2 days with mixture of 3 antagomirs (a, f, d) plus fluorescently labeled c (top panel); and for 3 days with mixture of all let-7 antagomirs (a, b, c, d, e, f, g, i and one fluorescently labeled a (bottom panel).
Figure 9:
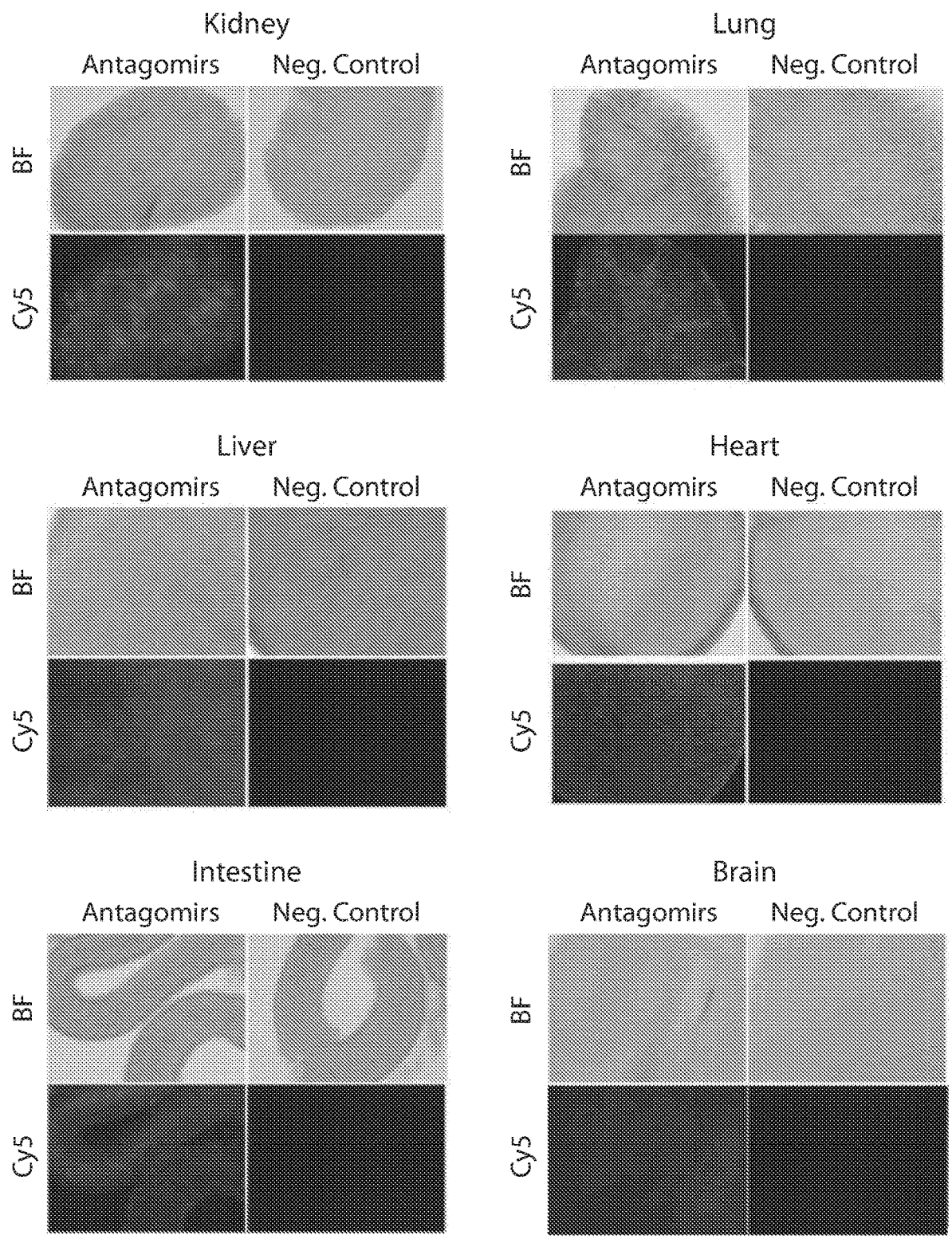
FIG. 9. Antagomirs In vivo. In vivo: Representative images of different organs after intrauterine Intraperitoneal injection of fluorescently labeled antagomir a (see FIG. 8) to E14.5 embryos.

Antagomirs are able to phenocopy both let7 cluster knockout and Lin28B overexpression. Genetic manipulation of the Lin28/let-7 axis revealed the enormous potential for therapeutic intervention. Next, let-7 in wild type mice was pharmacologically inhibited using antagomirs. Antagomirs are chemically engineered oligonucleotides that are efficient and specific silencers of endogenous microRNAs. Using an ex vivo organ culture of kidneys a statistically significant increase progenitors marked by Eya1 and Six2 was demonstrated (FIG. 8). To take the therapeutics to the next level fluorescently labeled antagomirs were administered in utero and it was found that several major organs such as heart, lung, intestines, brain, and kidney were able to uptake the antagomir against let-7a (FIG. 9). This invention outlines a new strategy to prolong or reactivate the period of nephrogenesis in newborns and holds great promise for children suffering from the complications of premature birth and/or intrauterine growth restriction.

Figure 12A:
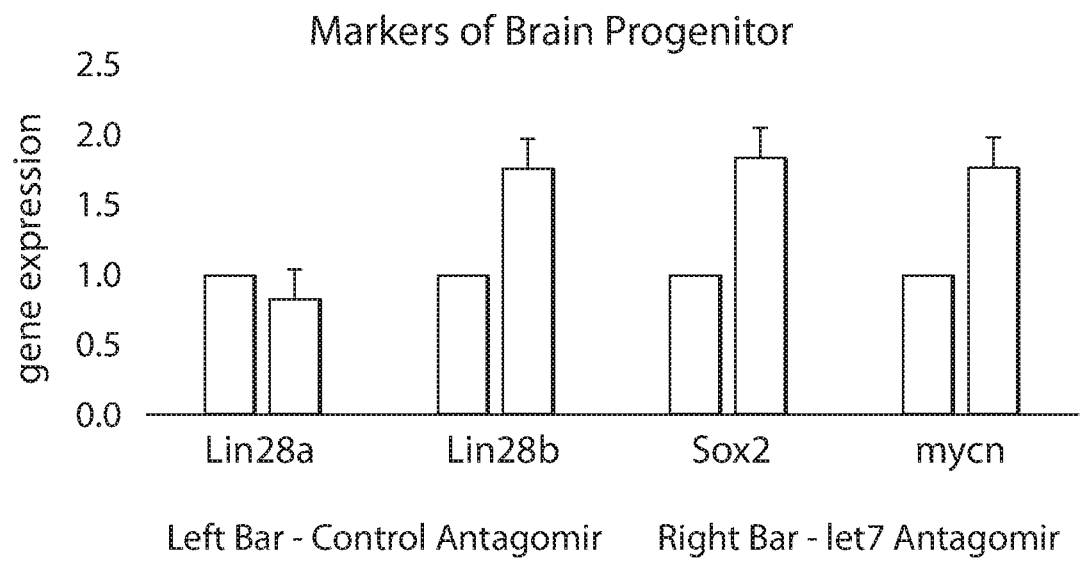
FIGS. 12A-12B. RT-PCR for Lin28a and Lin28b, Sox2, and Mycn in Brain (FIG. 12A) and Lin28a and Lin28b, Sox2 Lung.
Figure 12B:
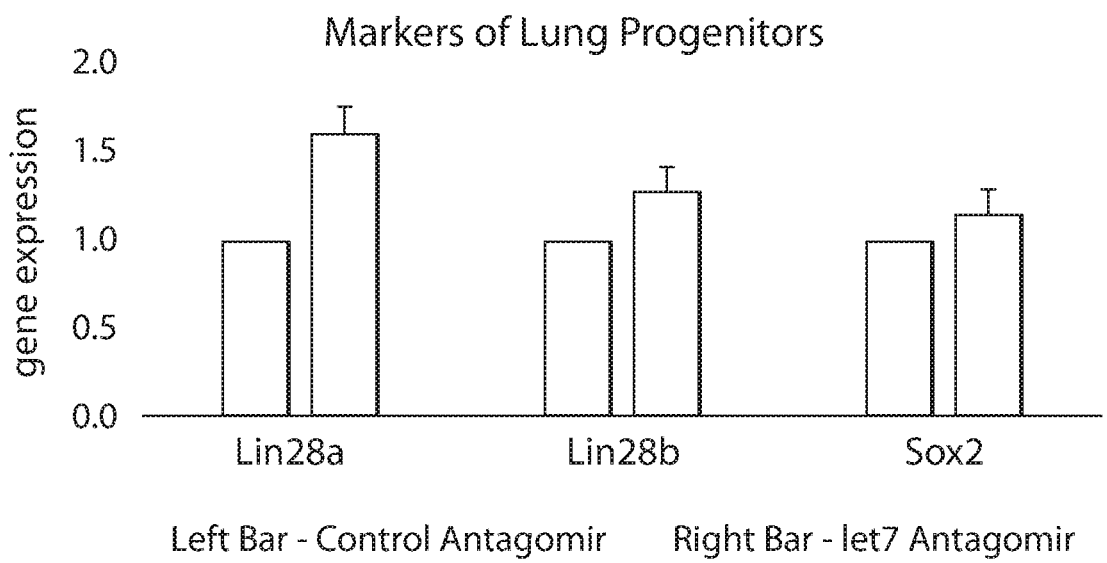

Similarly to ex vivo organ culture of kidneys, where statistically significant increase of progenitors marked by Eya1 and Six2 were observed (FIGS. 5A-5G), intraperitoneal injection of antagomirs to E14.5 embryos resulted in upregulation of let-7 targets as measured by Lin28a and Lin28b mRNA expression levels in the brain and in the lung (FIGS. 12A and 12B); as well as an increase in progenitors marked by Sox2 and Mycn in Brain and Sox2 in the lung (FIGS. 12A and 12B).

Materials and Methods
Animals

All animal work was done in accordance with IACUC guidelines at the ARCH facility in Children's Hospital Boston. The generation and maintenance of Col1a-TRE-LIN28B and Lin28bfl/fl animals was previously described (25-27). For transgene induction, 1 g/L doxycycline (Sigma) was administered to the drinking water at different time points to induce LIN28B transgene. Weanling mice were genotyped via ear clippings processed by Transnetyx. 9% casein diet was ordered from Envigo (TD.150207).

Intrauterine Injection of Antagomirs

Antagomirs against all 8 mature let-7 miRNAs were administered to individual E14.5 embryos by intrauterine-intraperitoneal injection, including a Cy5-labeled let-7a antagomir to facilitate localization tracing. On E14.5 of gestation, mice were anesthetized with isoflurane and a minilaparotomy procedure was performed to expose the uterine horns. E14.5 embryos received an intrauterine injection of antagomirs (or mirVana™ miRNA Inhibitor, Negative Control #1) with a total dose of 240 mg per kg body weight (diluted in PBS) each in a 25-µL volume by using a 33-gauge Hamilton syringe via intraperitoneal injection.

The following Anti-miR™ miRNA Inhibitors from Thermo Fisher Scientific (Cat. #4464088) were used: mmu-let-7a-5p, mmu-let-7b-5p, mmu-let-7c-5p, mmu-let-7d-5p, mmu-let-7e-5p, mmu-let-7f-5p, mmu-let-7g-5p, mmu-let-7i-5p, mirVana™ miRNA Inhibitor, Negative Control #1 (Thermo Fisher Scientific Cat #: 4464079 and 4464091), and Cy5-labeled mmu-let-let-7c mirVana™ miRNA Inhibitor (Thermo Fisher Scientific Cat #: 4464091)

Ex Vivo Organ Culture of Kidney

The ex vivo organ culture was performed as previously described (28) by treating wild type E 14.5 kidneys with the cocktail of all 8 antagomirs for 3 days at final concentration of 200 nM.

Quantitative RT-PCR (qRT-PCR)

RNA was isolated by TRIzol from whole organs and reverse-transcribed using a miScriptII RT kit (Qiagen, #218161). Relative mRNA expression was measured by qPCR using the $\Delta\Delta CT$ method with the following primers: mSix2 (forward primer, 5'-GCAAGTCAGCAACTGGTTCA-3'(SEQ ID NO: 1); reverse primer, 5'-CTTCTCATCCTCGGAACTGC-3' (SEQ ID NO: 2)), mEya1 (forward primer, 5'-TTTCCCTGGGAC-TACGAATG-3' (SEQ ID NO: 3); reverse primer, 5'-GGAAAGCCATCTGTTCCAAA-3' (SEQ ID NO: 4)), mbActin (forward primer, 5'-TACTCCTGCTTGCTGATC-CAC-3'(SEQ ID NO: 5); reverse primer, 5'-CAGAAGGAGATTACTGCTCTGGCT-3' (SEQ ID NO: 6)); and hLIN28B (forward primer, 5'-GCCCCTTGGATAT-TCCAGTC-3' (SEQ ID NO: 7); reverse primer, 5'-TGACT-CAAGGCCTTTGGAAG-3' (SEQ ID NO: 8)); mLin28b (forward primer, 5'-TTTGGCTGAGGAGGTAGACTG-CAT-3' (SEQ ID NO: 9); reverse primer 5'-ATGGATCA-GATGTGGACTGTGCGA-3') (SEQ ID NO: 10)); mLin28a (forward primer, 5'-AGCTTGCATTCCTTGGCATGATGG-3' (SEQ ID NO: 11); reverse primer-5'-AGGCGGTG-GAGTTCACCTTTAAGA-3') (SEQ ID NO: 12)). Primers for Sox2 and MycN were purchased from BioRad (PrimePCR SYBR).

Absolute quantification PCR was performed by using DNA standards ordered from IDT for amplicons of mLin28a and Lin28b primers. For qRT-PCR of mature and precursor let-7 miRNAs, Qiagen miScript target was used according to the manufacturer's instructions.

Immunoblot Analysis

Whole organs (from E12.5 to adulthood) were dissected and then lysed in RIPA buffer (Pierce) supplemented with protease inhibitor cocktail (Roche) and phosphatase inhibitor cocktail (Roche). Lysates were loaded and run on the 12% polyacrylamide gel (Bio-Rad) in 5x Laemmli sample buffer and transferred to a nitrocellulose membrane (GE Healthcare). The membrane was blocked for 1 h in PBST containing 5% milk and subsequently probed with primary antibodies overnight at 4° C. After 1-h incubation with sheep anti-mouse or donkey anti-rabbit HRP-conjugated secondary antibody (GE Healthcare), the protein level was detected with standard ECL reagents (Thermo Scientific). Antibodies used: anti-α/β-tubulin (Cell Signaling, #2148), anti-Lin28a (Cell Signaling, #3978), anti-Lin28b (mouse preferred) (Cell Signaling, #5422), anti-Six2 (Proteintech Group, #11562-1-AP).

Histological Analysis

Whole kidneys were fixed in 10% formalin overnight at room temperature, then placed in 70% ethanol and embedded in paraffin. Slides were dewaxed with xylene and rehydrated through a series of washes with decreasing percentages of ethanol. Antigen retrieval was performed in 10 mM sodium citrate buffer (pH 6.0) by placement in decloaking chamber for 45 minutes at 95° C. Slides were treated with 10% hydrogen peroxide to inhibit endogenous peroxidase activity. After blocking with 5% goat or rabbit serum (VECTASTAIN ABC kit #PK-6101), slides were incubated with primary antibody overnight at 4° C. and secondary antibody for 30 minutes at room temperature. Detection was performed with the VECTASTAIN Elite ABC Kit and DAB Substrate (Vector Laboratories, SK-4100). Sections were counterstained with hematoxylin for 20-30 seconds then dehydrated in increasing concentrations of ethanol before a 5-min incubation in xylene followed by mounting. Antibodies used: anti-LIN28B (Cell Signaling, #4196), anti-Six2 (Proteintech Group, #11562-1-AP), anti-Lef1 (Cell Signaling, #2230).

Immunofluorescence and Image Analysis

Whole kidneys were fixed in 4% PFA for half an hour at 4° C. then placed in PBS. Whole mount immunofluorescence, confocal microscopy, and optical projection tomography were carried out according to published protocols (29). Cell counts per niche (confocal) and niche counts (OPT) were performed as reported (29). Antibodies used: rabbit anti-Six2 (Proteintech Group, #11562-1-AP), anti-rabbit Alexa Fluor-658 conjugated secondary antibody (Life Technologies).

Blood Analysis

Renal panel tests performed on an Abaxis VetScan VS2 chemistry analyzer. Serum creatinine measured using isotope dilution LC-MS/MS in the O'Brien Core Center for Acute Kidney Injury Research, the University of Alabama at Birmingham School of Medicine.

Glomeruli Number Count

To compare the nephron number between transgenic and control mice, the number of glomerulus-like structures in 12 random fields from the kidney cortex were counted under 10× magnification.

Measurement Glomerular Filtration Rate (GFR)

GFR was measured using a high-throughput method described previously (29). Fluorescein isothiocyanate (FITC)-sinistrin (Fresenius Kabi, Linz, Austria) was administered to conscious mice under light anesthesia, isoflurane, via tail vein injections. Blood was collected from a small tail snip at 3, 7, 10, 15, 35, 55, and 75 min post-injection for the determination of FITC concentration by fluorescence. GFR was calculated by a two-phase exponential decay model 50.

Statistical Analysis

Data is expressed as mean±SD. Unpaired t-test with two-tailed distribution and Welch's correction was calculated using Prism (GraphPad Prism) to determine P-values. Statistical significance is displayed as P<0.05 (*), P<0.01 (**) unless specified otherwise.

Example 2

Figure 10A:
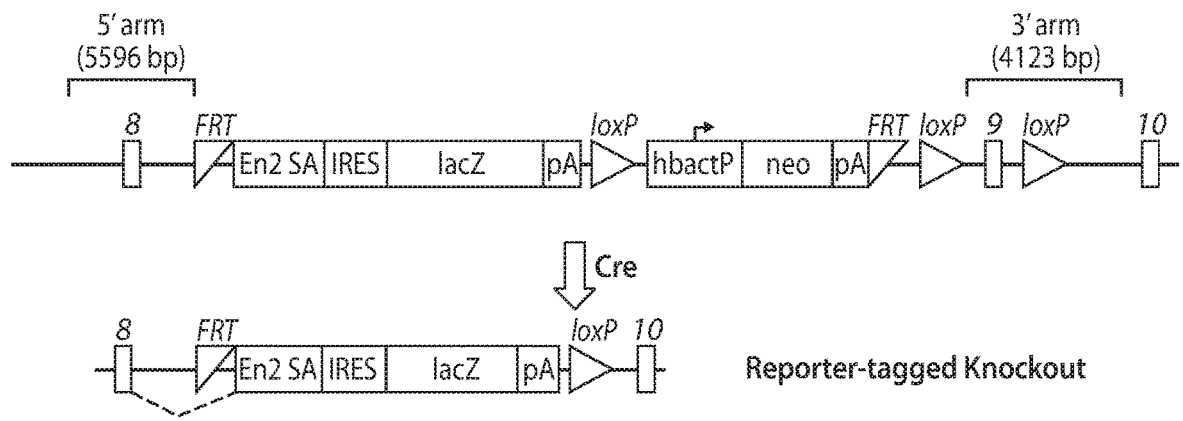
FIGS. 10A-10B. Targeting Dis3l2 locus in mice.
Figure 10B:
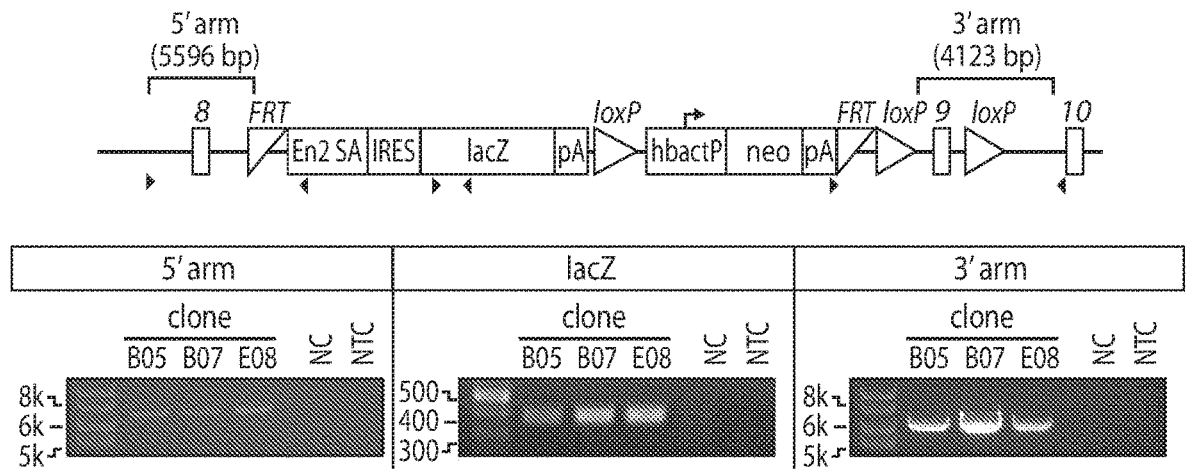
Figure 11A:
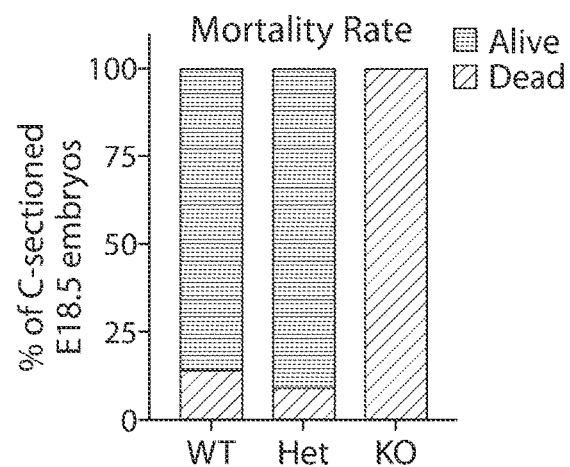
FIGS. 11A-11G. Dis3l2 knockout mouse model.
Figure 11B:
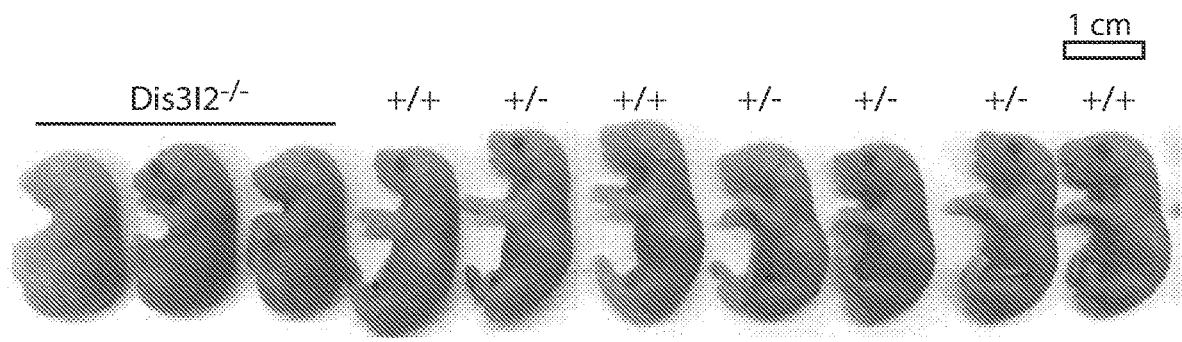
Figure 11C:
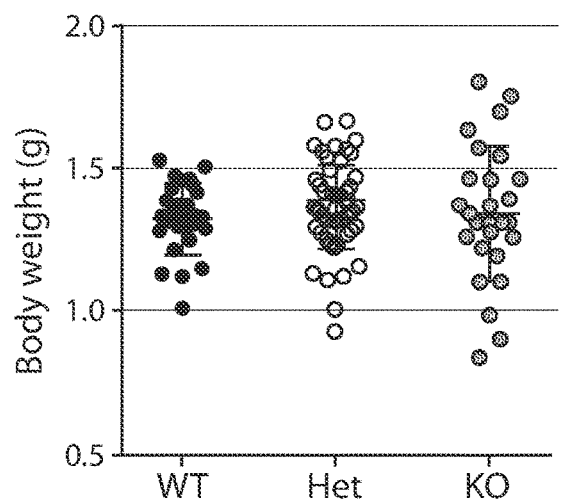
Figure 11D:
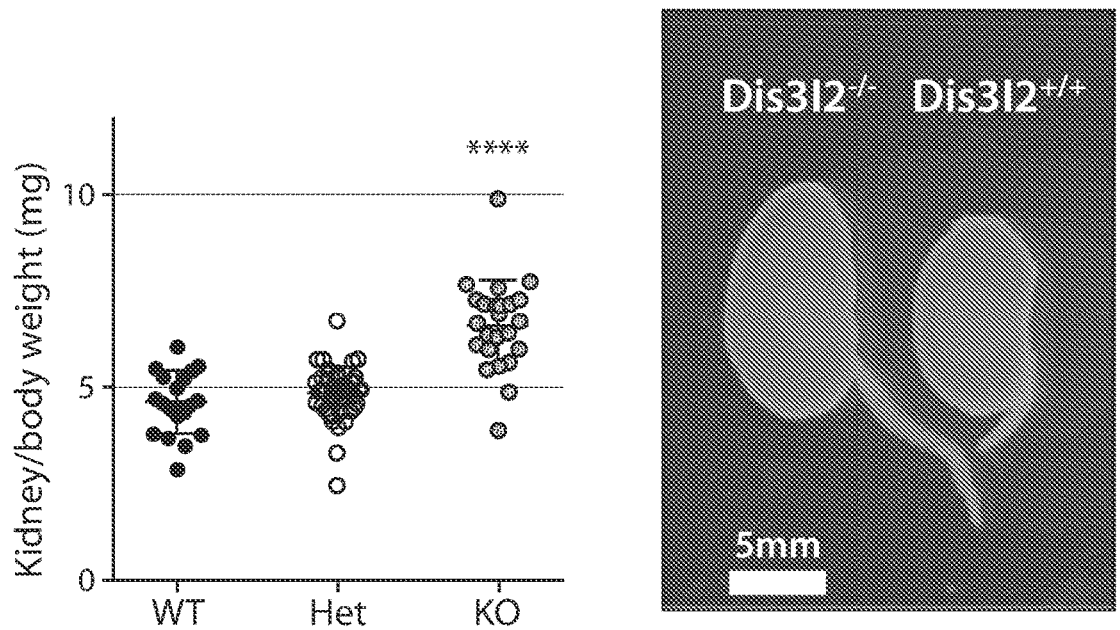
Figure 11E:
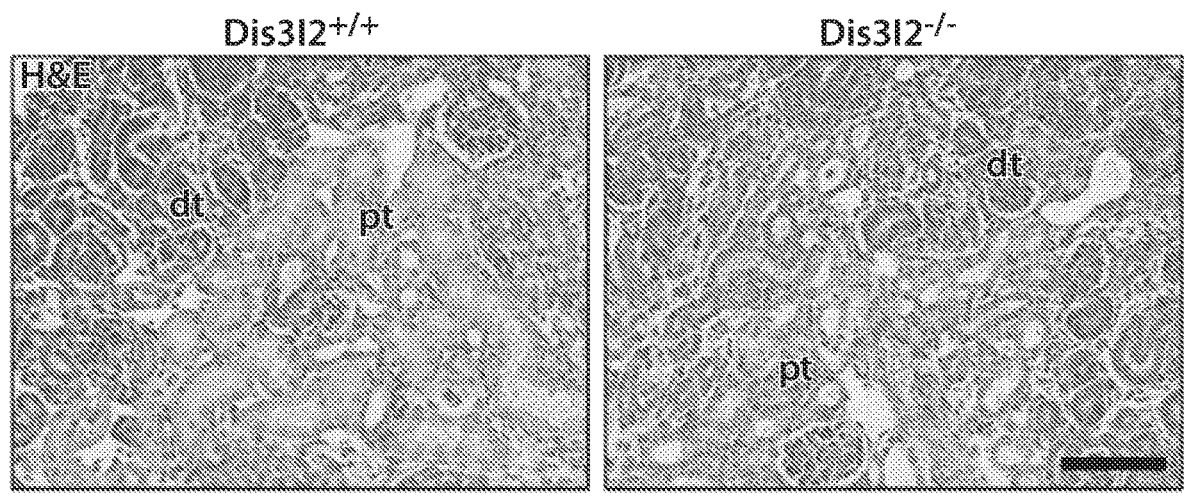
Figure 11F:
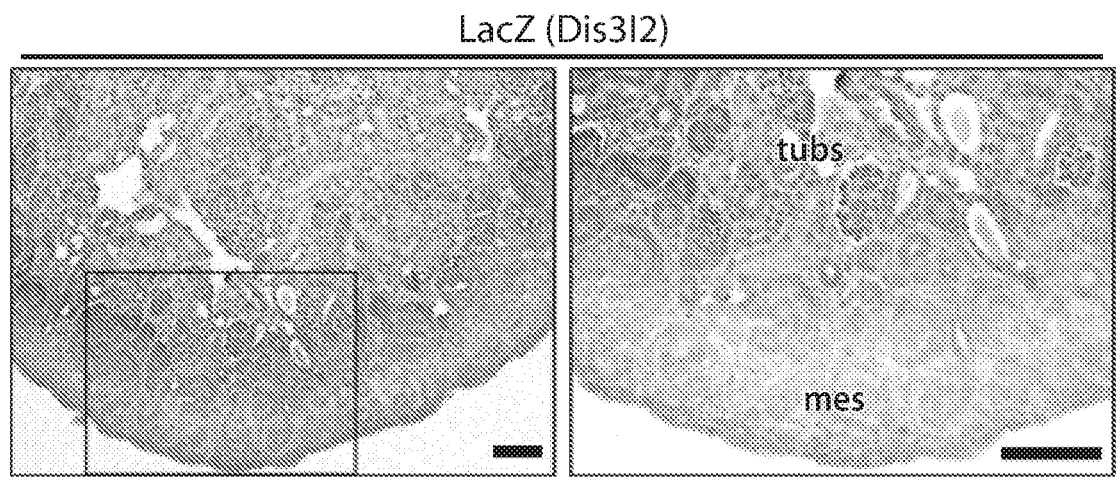
Figure 11G:
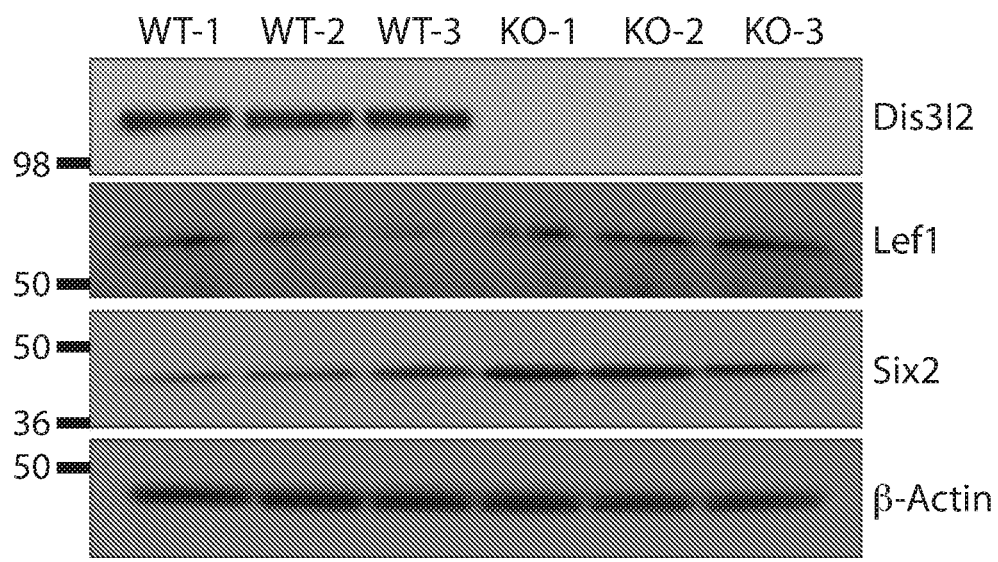

Dis312 is an RNA exonuclease that degrades let-7 precursors (pre-let-7), making this gene a critical component of the pathway. Based on in vitro functional studies and mutational associations in humans, the loss of Dis312 phenocopies effects of Lin28 overexpression (21, 22). To understand the in vivo function of Dis312, a mouse strain harboring a constitutive knockout of Dis312 was generated by crossing females carrying the Vasa-Cre allele to Dis312 (exon 9-foxed) transgenic males (see Methods). The cross resulted in constitutional deletion of Dis312 in all tissues by virtue of Cre expression in oocytes (23) (FIGS. 10A and 10B). Although born with expected Mendelian ratios, 100% of Dis312 knockout neonates died within the first hour after birth (data not shown). All the C-sectioned day 18.5 (E18.5) knockout embryos (~1 day prior to their birth) started breathing but died within few minutes (FIGS. 11A and 11B). No significant difference was observed in the body weight between Dis312 knockout, wild type and heterozygous littermates at E18.5 (FIG. 11C). However, Dis312 knockout kidneys were significantly larger in weight and size compared to controls (FIG. 11D). LacZ immunohistochemistry was used to monitor Dis312 expression in the transgenic E18.5 kidneys. Dis312 was expressed solely in the distal and proximal tubules and it was absent in peripheral mesenchymal cells (FIG. 11E). Moreover, Dis312 knockout kidneys contained more renal progenitor proteins as measured by Six2 and Lef1 (FIGS. 11F and 11G) phenocopying effects of Lin28 overexpression and let-7 suppression on upregulation of progenitor cells.

Methods

Animals

All animal work was done in accordance with IACUC guidelines at the ARCH facility in Children's Hospital Boston. Weanling mice were genotyped via ear clippings processed by Transnetyx.

Dis312 transgenic mouse model. Targeted mESCs (Dis312$^{tm1a(EUCOMM)Hmgu}$) were obtained from Helmholtz Zentrum Munchen via the European Conditional Mouse Mutagenesis Program (EUCOMM)(24). Three independent clones were validated by PCR-based genotyping using the specific primers (Table 1). The gene targeted ESCs were injected into chimeric blastocysts. Once injected, they were implanted into pseudopregnant Balb/c females and mutant mice were established. To determine if the strain has gone germline, chimeras were crossed with wild-type mice, the offspring were screened, and several Dis312 transgenic animals were confirmed of germline transmission. The Dis312 transgenic knockout strains were then expanded.

Constitutive knockout of Dis312 was generated by crossing females carrying Vasa-Cre allele (Jackson laboratory, stock #006954) to Dis312 transgenic males. Dis312 knockout embryos were harvested by caesarian-section at 18.5 days post coitum.

TABLE 1

Primers for genotyping Dis3L2 knockout

| Name | Sequence | Description |
|---|---|---|
| LAR3 | CACAACGGGTTCTTCTGTTAGTCC (SEQ ID NO: 13) | 5' arm universal |

TABLE 1-continued

Primers for genotyping Dis3L2 knockout

| Name | Sequence | Description |
|---|---|---|
| Dis312-GF4 | CAGGTCCATGCTGGTATTGCATTGCTC (SEQ ID NO: 14) | 5' arm gene-specific |
| Dis312-GF3 | CATGCTGGTATTGCATTGCTCTGTCAGCAG (SEQ ID NO: 15) | 5' arm gene-specific |
| RAF5 | CACACCTCCCCCTGAACCTGAAAC (SEQ ID NO: 16) | 3' arm universal |
| Dis312-GR4 | CAATGCTGCAATCCATTCTCTCCACCTCAC (SEQ ID NO: 17) | 3' arm gene-specific |
| Dis312-GR3 | CAACCTTCTCCACTGCATACCACGGCAATC (SEQ ID NO: 18) | 3' arm gene-specific |

Immunoblot Analysis

Whole E18.5 kidneys were dissected and then lysed in RIPA buffer (Pierce) supplemented with protease inhibitor cocktail (Roche) and phosphatase inhibitor cocktail (Roche). Lysates were loaded and run on the 12% polyacrylamide gel (Bio-Rad) in 5× Laemmli sample buffer and transferred to a nitrocellulose membrane (GE Healthcare). The membrane was blocked for 1 h in PBST containing 5% milk and subsequently probed with primary antibodies overnight at 4° C. After 1 h incubation with sheep anti-mouse or donkey anti-rabbit HRP-conjugated secondary antibody (GE Healthcare), the protein level was detected with standard ECL reagents (Thermo Scientific). The following antibodies were used: Rabbit anti-Lef1 (Cell signaling, #2230); Rabbit anti-Six2 (Proteintech Group, #11562-1-AP);

Histological Analysis

Tissue samples were fixed in 10% buffered formalin and embedded in paraffin. Immunostaining was performed using the following antibody: Anti-galactosidase (ab4761, Abcam) at 1:250 dilution. Slides were dewaxed with xylene and rehydrated through a series of washes with decreasing percentages of ethanol. Antigen retrieval was performed in 10 mM sodium citrate buffer (pH 6.0) by placement in decloaking chamber for 30 minutes at 95° C. Immunohistochemistry was performed with Elite ABC kit and DAB substrate (Vector Laboratories) according to the manufacturer's protocol.

REFERENCES

1. Polesskaya, A., Cuvellier, S., Naguibneva, I., Duquet, A., Moss, E. G. & Harel-Bellan, A. Lin-28 binds IGF-2 mRNA and participates in skeletal myogenesis by increasing translation efficiency. *Genes Dev* 21, 1125-38 (2007).
2. Xu, B. & Huang, Y. Histone H2a mRNA interacts with Lin28 and contains a Lin28-dependent posttranscriptional regulatory element. *Nucleic Acids Res* 37, 4256-63 (2009).
3. Qiu, C., Ma, Y., Wang, J., Peng, S. & Huang, Y. Lin28-mediated post-transcriptional regulation of Oct4 expression in human embryonic stem cells. *Nucleic Acids Res* 38, 1240-8 (2010).
4. Peng, S., Chen, L. L., Lei, X. X., Yang, L., Lin, H., Carmichael, G. G. & Huang, Y. Genome-wide studies reveal that Lin28 enhances the translation of genes important for growth and survival of human embryonic stem cells. *Stem Cells* 29, 496-504 (2011).
5. Wilbert, M. L., Huelga, S. C., Kapeli, K., Stark, T. J., Liang, T. Y., Chen, S. X., Yan, B. Y., Nathanson, J. L., Hutt, K. R., Lovci, M. T., Kazan, H., Vu, A. Q., Massirer, K. B., Morris, Q., Hoon, S. & Yeo, G. W. LIN28 binds messenger RNAs at GGAGA motifs and regulates splicing factor abundance. *Mol Cell* 48, 195-206 (2012).
6. Heo, I., Joo, C., Cho, J., Ha, M., Han, J. & Kim, V. N. Lin28 mediates the terminal uridylation of let-7 precursor MicroRNA. *Molecular cell* 32, 276-84 (2008).
7. Rybak, A., Fuchs, H., Smirnova, L., Brandt, C., Pohl, E. E., Nitsch, R. & Wulczyn, F. G. A feedback loop comprising lin-28 and let-7 controls pre-let-7 maturation during neural stem-cell commitment. *Nature cell biology* 10, 987-93 (2008).
8. Viswanathan, S. R., Daley, G. Q. & Gregory, R. I. Selective blockade of microRNA processing by Lin28. *Science* 320, 97-100 (2008).
9. Shinoda, G., Shyh-Chang, N., Soysa, T. Y., Zhu, H., Seligson, M. T., Shah, S. P., Abo-Sido, N., Yabuuchi, A., Hagan, J. P., Gregory, R. I., Asara, J. M., Cantley, L. C., Moss, E. G. & Daley, G. Q. Fetal deficiency of 1 in28 programs life-long aberrations in growth and glucose metabolism. *Stem Cells* 31, 1563-73 (2013).
10. Yang, D. H. & Moss, E. G. Temporally regulated expression of Lin-28 in diverse tissues of the developing mouse. *Gene Expr Patterns* 3, 719-26 (2003).
11. Keller, G., Zimmer, G., Mall, G., Ritz, E. & Amann, K. Nephron number in patients with primary hypertension. *N Engl J Med* 348, 101-8 (2003).
12. Hoy, W. E., Hughson, M. D., Bertram, J. F., Douglas-Denton, R. & Amann, K. Nephron number, hypertension, renal disease, and renal failure. *J Am Soc Nephrol* 16, 2557-64 (2005).
13. Abitbol, C. L., Chandar, J., Rodriguez, M. M., Berho, M., Seeherunvong, W., Freundlich, M. & Zilleruelo, G. Obesity and preterm birth: additive risks in the progression of kidney disease in children. *Pediatr Nephrol* 24, 1363-70 (2009).
14. Taguchi, A., Kaku, Y., Ohmori, T., Sharmin, S., Ogawa, M., Sasaki, H. & Nishinakamura, R. Redefining the in vivo origin of metanephric nephron progenitors enables generation of complex kidney structures from pluripotent stem cells. *Cell Stem Cell* 14, 53-67 (2014).
15. Takasato, M., Er, P. X., Becroft, M., Vanslambrouck, J. M., Stanley, E. G., Elefanty, A. G. & Little, M. H. Directing human embryonic stem cell differentiation towards a renal lineage generates a self-organizing kidney. *Nat Cell Biol* 16, 118-26 (2014).
16. Lam, A. Q., Freedman, B. S., Morizane, R., Lerou, P. H., Valerius, M. T. & Bonventre, J. V. Rapid and efficient differentiation of human pluripotent stem cells into intermediate mesoderm that forms tubules expressing kidney proximal tubular markers. *J Am Soc Nephrol* 25, 1211-25 (2014).
17. Yokoo, T., Fukui, A. & Kobayashi, E. Application of regenerative medicine for kidney diseases. *Organogenesis* 3, 34-43 (2007).
18. Lloyd, L. J., Foster, T., Rhodes, P., Rhind, S. M. & Gardner, D. S. Protein-energy malnutrition during early gestation in sheep blunts fetal renal vascular and nephron development and compromises adult renal function. *J Physiol* 590, 377-93 (2012).
19. Li, J., Khodus, G. R., Kruusmagi, M., Kamali-Zare, P., Liu, X. L., Eklof, A. C., Zelenin, S., Brismar, H. & Aperia, A. Ouabain protects against adverse developmental programming of the kidney. *Nat Commun* 1, 42 (2010).
20. Tu, H. C., Schwitalla, S., Qian, Z., LaPier, G. S., Yermalovich, A., Ku, Y. C., Chen, S. C., Viswanathan, S. R., Zhu, H., Nishihara, R., et al. (2015). LIN28 cooperates with WNT signaling to drive invasive intestinal and colorectal adenocarcinoma in mice and humans. Genes & development 29, 1074-1086.
21. H. M. Chang, R. Triboulet, J. E. Thornton, R. I. Gregory, A role for the Perlman syndrome exonuclease Dis3l2 in the Lin28-let-7 pathway. Nature 497, 244 (May 9, 2013).
22. D. Astuti et al., Germline mutations in DIS3L2 cause the Perlman syndrome of overgrowth and Wilms tumor susceptibility. Nature genetics 44, 277 (March, 2012).
23. T. Gallardo, L. Shirley, G. B. John, D. H. Castrillon, Generation of a germ cell-specific mouse transgenic Cre line, Vasa-Cre. Genesis 45, 413 (June, 2007).
24. W. C. Skarnes et al., A conditional knockout resource for the genome-wide study of mouse gene function. Nature 474, 337 (Jun. 15, 2011).25. H. Zhu et al., Lin28a transgenic mice manifest size and puberty phenotypes identified in human genetic association studies. Nat Genet 42, 626 (July, 2010).
26. W. Zhou, C. R. Freed, Adenoviral gene delivery can reprogram human fibroblasts to induced pluripotent stem cells. Stem cells 27, 2667 (November, 2009).
27. H. Zhu et al., The Lin28/let-7 axis regulates glucose metabolism. Cell 147, 81 (Sep. 30, 2011).
28. H. Barak, S. C. Boyle, Organ culture and immunostaining of mouse embryonic kidneys. Cold Spring Harbor protocols 2011, pdb prot5558 (Jan. 1, 2011).
29. A. N. Combes et al., An integrated pipeline for the multidimensional analysis of branching morphogenesis. Nature protocols 9, 2859 (December, 2014).

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the disclosure encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

Where websites are provided, URL addresses are provided as non-browser-executable codes, with periods of the respective web address in parentheses. The actual web addresses do not contain the parentheses.

In addition, it is to be understood that any particular embodiment of the present disclosure may be explicitly excluded from any one or more of the claims. Where ranges are given, any value within the range may explicitly be excluded from any one or more of the claims. Any embodiment, element, feature, application, or aspect of the compositions and/or methods of the disclosure, can be excluded from any one or more claims. For purposes of brevity, all of the embodiments in which one or more elements, features, purposes, or aspects is excluded are not set forth explicitly herein.

What is claimed is:

1. A method of prolonging or reactivating kidney organogenesis, the method comprising administering to a subject in need thereof an effective amount of an agent that inhibits the expression or activity of let-7a, let-7d, and let-7f microRNAs.

2. The method of claim 1, wherein the agent inhibits expression of the let-7a, let-7d, and let-7f microRNAs.

3. The method of claim 1, wherein the subject is human.

4. The method of claim 1, wherein the subject is malnourished.

5. The method of claim 1, wherein the agent is delivered systemically or directly to a kidney.

6. The method of claim 1, wherein the agent inhibits the expression or activity of let-7a, let-7d, and let-7f microRNAs systemically or in the kidney.

7. The method of claim 1, wherein the agent increases the number of functional nephrons in the kidney.

8. The method of claim 1, wherein the agent improves kidney function.

9. A method of prolonging organogenesis in an embryonic kidney, the method comprising inhibiting the expression or activity of let-7a, let-7d, and let-7f microRNAs in the embryonic kidney.

10. The method of claim 1, wherein the agent comprises one or more antagomirs.

* * * * *